(12) United States Patent
Galloway et al.

(10) Patent No.: US 9,254,095 B2
(45) Date of Patent: Feb. 9, 2016

(54) ELECTROCARDIOGRAM SIGNAL DETECTION

(71) Applicant: AliveCor, Inc, San Francisco, CA (US)

(72) Inventors: Conner Daniel Cross Galloway, Colorado Springs, CO (US); David E. Albert, Oklahoma City, OK (US)

(73) Assignee: ALIVECOR, San Francisco, CA (US)

( * ) Notice: Subject to any disclaimer, the term of this patent is extended or adjusted under 35 U.S.C. 154(b) by 0 days.

(21) Appl. No.: 14/076,076

(22) Filed: Nov. 8, 2013

(65) Prior Publication Data

US 2014/0128758 A1 May 8, 2014

Related U.S. Application Data

(60) Provisional application No. 61/723,788, filed on Nov. 8, 2012, provisional application No. 61/802,091, filed on Mar. 15, 2013.

(51) Int. Cl.
*A61B 5/044* (2006.01)
*A61B 5/00* (2006.01)
(Continued)

(52) U.S. Cl.
CPC .............. *A61B 5/044* (2013.01); *A61B 5/0472* (2013.01); *A61B 5/7203* (2013.01); *A61B 5/0404* (2013.01); *A61B 5/046* (2013.01); *A61B 5/0464* (2013.01)

(58) Field of Classification Search
CPC .... A61B 5/0452; A61B 5/0456; A61B 5/046; A61B 5/0472; A61B 5/7203; A61B 5/7246; A61B 5/7264; A61B 5/37258; A61N 1/37258
USPC .................................. 600/516, 517, 518, 521
See application file for complete search history.

(56) References Cited

U.S. PATENT DOCUMENTS

| 3,717,857 A | 2/1973 | Evans |
|---|---|---|
| 3,731,311 A | 5/1973 | Williams |

(Continued)

FOREIGN PATENT DOCUMENTS

| CH | 675675 A5 | 10/1990 |
|---|---|---|
| CN | 101828915 A | 9/2010 |

(Continued)

OTHER PUBLICATIONS

Albert, David E.; U.S. Appl. No. 14/252,044 entitled "Cardiac performance monitoring system for use with mobile communications devices," filed Apr. 14, 2014.

(Continued)

*Primary Examiner* — Christopher A Flory
(74) *Attorney, Agent, or Firm* — Wilson Sonsini Goodrich & Rosati

(57) ABSTRACT

Apparatuses and methods for extracting, de-noising, and analyzing electrocardiogram signals. Any of the apparatuses described herein may be implemented as a (or as part of a) computerized system. For example, described herein are apparatuses and methods of using them or performing the methods, for extracting and/or de-noising ECG signals from a starting signal. Also described herein are apparatuses and methods for analyzing an ECG signal, for example, to generate one or more indicators or markers of cardiac fitness, including in particular indicators of atrial fibrillation. Described herein are apparatuses and method for determining if a patient is experiencing a cardiac event, such as an arrhythmia.

42 Claims, 10 Drawing Sheets
(2 of 10 Drawing Sheet(s) Filed in Color)

(51) Int. Cl.
*A61B 5/0472* (2006.01)
*A61B 5/046* (2006.01)
*A61B 5/0404* (2006.01)
*A61B 5/0464* (2006.01)

(56) References Cited

U.S. PATENT DOCUMENTS

| | | | |
|---|---|---|---|
| 3,768,014 A | 10/1973 | Smith et al. | |
| 3,776,228 A | 12/1973 | Semler | |
| 3,779,237 A | 12/1973 | Goeltz et al. | |
| 3,779,249 A | 12/1973 | Semler | |
| 3,782,367 A | 1/1974 | Hochberg et al. | |
| 3,805,227 A | 4/1974 | Lester | |
| 3,882,277 A | 5/1975 | DePedro et al. | |
| 3,885,552 A | 5/1975 | Kennedy | |
| 3,898,984 A | 8/1975 | Mandel et al. | |
| 3,909,599 A | 9/1975 | Trott, Jr. et al. | |
| 4,027,146 A | 5/1977 | Gilmore | |
| 4,045,767 A | 8/1977 | Nishihara et al. | |
| 4,083,366 A | 4/1978 | Gombrich et al. | |
| 4,095,050 A | 6/1978 | Beachem et al. | |
| 4,221,223 A | 9/1980 | Linden | |
| 4,230,127 A | 10/1980 | Larson | |
| 4,231,031 A | 10/1980 | Crowther et al. | |
| 4,250,888 A | 2/1981 | Grosskopf | |
| 4,281,664 A | 8/1981 | Duggan | |
| 4,295,472 A | 10/1981 | Adams | |
| 4,312,358 A | 1/1982 | Barney | |
| 4,318,130 A | 3/1982 | Heuer | |
| 4,364,397 A | 12/1982 | Citron et al. | |
| 4,367,752 A | 1/1983 | Jimenez et al. | |
| 4,409,984 A | 10/1983 | Dick | |
| 4,531,527 A | 7/1985 | Reinhold, Jr. et al. | |
| 4,567,883 A | 2/1986 | Langer et al. | |
| 4,572,182 A | 2/1986 | Royse | |
| 4,580,250 A | 4/1986 | Kago et al. | |
| 4,583,553 A | 4/1986 | Shah et al. | |
| 4,622,979 A | 11/1986 | Katchis et al. | |
| 4,625,730 A | 12/1986 | Fountain et al. | |
| 4,630,204 A * | 12/1986 | Mortara | 600/516 |
| 4,803,625 A | 2/1989 | Fu et al. | |
| 4,889,131 A | 12/1989 | Salem et al. | |
| 4,920,489 A | 4/1990 | Hubelbank et al. | |
| 4,938,228 A | 7/1990 | Righter et al. | |
| 4,938,229 A | 7/1990 | Bergelson et al. | |
| 4,958,641 A | 9/1990 | Digby et al. | |
| 4,977,899 A | 12/1990 | Digby et al. | |
| 4,981,141 A | 1/1991 | Segalowitz | |
| 5,012,814 A | 5/1991 | Mills et al. | |
| 5,023,906 A | 6/1991 | Novas | |
| 5,025,794 A | 6/1991 | Albert et al. | |
| 5,058,597 A | 10/1991 | Onoda et al. | |
| 5,090,418 A | 2/1992 | Squires et al. | |
| 5,111,396 A | 5/1992 | Mills et al. | |
| 5,128,552 A | 7/1992 | Fang et al. | |
| 5,136,555 A | 8/1992 | Gardos | |
| 5,181,519 A | 1/1993 | Bible | |
| 5,191,891 A | 3/1993 | Righter | |
| 5,201,321 A | 4/1993 | Fulton | |
| 5,218,969 A | 6/1993 | Bredesen et al. | |
| 5,226,424 A | 7/1993 | Bible | |
| 5,238,001 A | 8/1993 | Gallant et al. | |
| D341,659 S | 11/1993 | Homayoun et al. | |
| 5,259,387 A | 11/1993 | Depinto | |
| 5,289,824 A | 3/1994 | Mills et al. | |
| 5,301,679 A | 4/1994 | Taylor | |
| 5,304,186 A | 4/1994 | Semler et al. | |
| 5,313,953 A | 5/1994 | Yomtov et al. | |
| 5,317,269 A | 5/1994 | Mills et al. | |
| 5,321,618 A | 6/1994 | Gessman | |
| 5,333,616 A | 8/1994 | Mills et al. | |
| 5,336,245 A | 8/1994 | Adams et al. | |
| 5,337,752 A | 8/1994 | Reeves | |
| 5,339,824 A | 8/1994 | Engira | |
| 5,343,869 A | 9/1994 | Pross et al. | |
| 5,343,870 A | 9/1994 | Gallant et al. | |
| 5,348,008 A | 9/1994 | Bornn et al. | |
| 5,351,695 A | 10/1994 | Mills et al. | |
| 5,360,005 A | 11/1994 | Wilk | |
| 5,365,935 A | 11/1994 | Righter et al. | |
| 5,410,587 A | 4/1995 | Grunwell | |
| 5,417,222 A | 5/1995 | Dempsey et al. | |
| 5,433,736 A | 7/1995 | Nilsson | |
| 5,452,356 A | 9/1995 | Albert | |
| 5,466,246 A | 11/1995 | Silvian | |
| 5,467,773 A | 11/1995 | Bergelson et al. | |
| 5,481,255 A | 1/1996 | Albert et al. | |
| 5,503,158 A | 4/1996 | Coppock et al. | |
| 5,518,001 A | 5/1996 | Snell | |
| 5,522,396 A | 6/1996 | Langer et al. | |
| 5,539,705 A | 7/1996 | Akerman et al. | |
| D372,785 S | 8/1996 | Sabri et al. | |
| 5,544,661 A | 8/1996 | Davis et al. | |
| 5,551,953 A | 9/1996 | Lattin et al. | |
| 5,561,712 A | 10/1996 | Nishihara | |
| 5,568,448 A | 10/1996 | Tanigushi et al. | |
| 5,579,284 A | 11/1996 | May | |
| 5,583,758 A | 12/1996 | McIlroy et al. | |
| D377,983 S | 2/1997 | Sabri et al. | |
| 5,608,723 A | 3/1997 | Felsenstein | |
| 5,613,495 A | 3/1997 | Mills et al. | |
| 5,634,468 A | 6/1997 | Platt et al. | |
| 5,652,570 A | 7/1997 | Lepkofker | |
| 5,661,699 A | 8/1997 | Sutton | |
| 5,675,325 A | 10/1997 | Taniguchi et al. | |
| 5,678,562 A | 10/1997 | Sellers | |
| 5,701,894 A | 12/1997 | Cherry et al. | |
| 5,704,364 A | 1/1998 | Saltzstein et al. | |
| 5,724,025 A | 3/1998 | Tavori | |
| 5,730,143 A | 3/1998 | Schwarzberg | |
| 5,735,285 A | 4/1998 | Albert et al. | |
| 5,742,251 A | 4/1998 | Gerber | |
| 5,748,103 A | 5/1998 | Flach et al. | |
| 5,758,654 A * | 6/1998 | Burton-Krahn et al. | 600/517 |
| 5,764,763 A | 6/1998 | Jensen et al. | |
| 5,772,586 A | 6/1998 | Heinonen et al. | |
| 5,818,788 A | 10/1998 | Kimura et al. | |
| 5,825,718 A | 10/1998 | Ueki et al. | |
| 5,827,179 A | 10/1998 | Lichter et al. | |
| 5,840,020 A | 11/1998 | Heinonen et al. | |
| 5,844,997 A | 12/1998 | Murphy, Jr. | |
| 5,861,018 A | 1/1999 | Feierbach | |
| 5,873,369 A | 2/1999 | Laniado et al. | |
| 5,876,351 A | 3/1999 | Rohde | |
| 5,877,675 A | 3/1999 | Rebstock et al. | |
| 5,889,730 A | 3/1999 | May | |
| 5,908,383 A | 6/1999 | Brynjestad | |
| 5,929,761 A | 7/1999 | Van Der Laan et al. | |
| 5,941,829 A | 8/1999 | Saltzstein et al. | |
| 5,954,640 A | 9/1999 | Szabo | |
| D414,870 S | 10/1999 | Saltzstein et al. | |
| 5,970,388 A | 10/1999 | Will | |
| 5,976,083 A | 11/1999 | Richardson et al. | |
| 5,982,297 A | 11/1999 | Welle | |
| 5,983,127 A | 11/1999 | Depinto | |
| 6,008,703 A | 12/1999 | Perrott et al. | |
| 6,014,631 A | 1/2000 | Teagarden et al. | |
| 6,024,699 A | 2/2000 | Surwit et al. | |
| 6,024,705 A | 2/2000 | Schlager et al. | |
| 6,037,704 A | 3/2000 | Welle | |
| 6,039,688 A | 3/2000 | Douglas et al. | |
| 6,048,319 A | 4/2000 | Hudgins et al. | |
| D427,315 S | 6/2000 | Saltzstein et al. | |
| 6,072,396 A | 6/2000 | Gaukel | |
| 6,083,248 A | 7/2000 | Thompson | |
| 6,084,510 A | 7/2000 | Lemelson et al. | |
| 6,100,806 A | 8/2000 | Gaukel | |
| 6,102,856 A | 8/2000 | Groff et al. | |
| 6,126,596 A | 10/2000 | Freedman | |
| 6,153,532 A | 11/2000 | Dow et al. | |
| 6,159,147 A | 12/2000 | Lichter et al. | |
| 6,171,256 B1 | 1/2001 | Joo et al. | |
| 6,198,394 B1 | 3/2001 | Jacobsen et al. | |
| 6,223,164 B1 | 4/2001 | Seare et al. | |

(56) References Cited

U.S. PATENT DOCUMENTS

| | | |
|---|---|---|
| 6,224,548 B1 | 5/2001 | Gopinathan et al. |
| 6,236,889 B1 | 5/2001 | Soykan et al. |
| 6,264,614 B1 | 7/2001 | Albert et al. |
| 6,282,440 B1 | 8/2001 | Brodnick et al. |
| 6,282,441 B1 | 8/2001 | Raymond et al. |
| 6,289,238 B1 | 9/2001 | Besson et al. |
| 6,319,201 B1 | 11/2001 | Wilk |
| 6,343,049 B1 | 1/2002 | Toda |
| 6,363,139 B1 | 3/2002 | Zurek et al. |
| 6,364,834 B1 | 4/2002 | Reuss et al. |
| 6,366,871 B1 | 4/2002 | Geva |
| 6,377,843 B1 | 4/2002 | Naydenov et al. |
| 6,418,394 B1 | 7/2002 | Puolakanaho et al. |
| 6,433,689 B1 | 8/2002 | Hovind et al. |
| 6,453,164 B1 | 9/2002 | Fuller et al. |
| 6,478,736 B1 | 11/2002 | Mault |
| 6,507,734 B1 | 1/2003 | Berger et al. |
| 6,513,532 B2 | 2/2003 | Mault et al. |
| 6,549,756 B1 | 4/2003 | Engstrom |
| 6,558,320 B1 | 5/2003 | Causey et al. |
| 6,579,231 B1 | 6/2003 | Phipps |
| 6,595,929 B2 | 7/2003 | Stivoric et al. |
| 6,600,471 B2 | 7/2003 | Lee et al. |
| 6,605,038 B1 | 8/2003 | Teller et al. |
| 6,612,985 B2 | 9/2003 | Eiffert et al. |
| 6,616,613 B1 | 9/2003 | Goodman |
| 6,636,761 B2 | 10/2003 | Brodnick |
| 6,685,633 B2 | 2/2004 | Albert et al. |
| 6,717,983 B1 | 4/2004 | Toda |
| 6,790,178 B1 | 9/2004 | Mault et al. |
| 6,804,558 B2 | 10/2004 | Haller et al. |
| 6,820,057 B1 | 11/2004 | Loch et al. |
| 6,845,263 B2 | 1/2005 | Kawaguchi |
| 6,893,396 B2 | 5/2005 | Schulze et al. |
| 6,928,535 B2 | 8/2005 | Yamashita et al. |
| 6,950,681 B2 | 9/2005 | Hofmann |
| 6,970,737 B1 | 11/2005 | Brodnick et al. |
| 6,987,965 B2 | 1/2006 | Ng et al. |
| 7,009,511 B2 | 3/2006 | Mazar et al. |
| 7,018,339 B2 | 3/2006 | Birnbaum et al. |
| 7,020,508 B2 | 3/2006 | Stivoric et al. |
| 7,031,745 B2 | 4/2006 | Shen |
| 7,061,381 B2 | 6/2006 | Forcier et al. |
| 7,103,407 B2 | 9/2006 | Hjelt et al. |
| 7,107,095 B2 | 9/2006 | Manolas |
| 7,108,659 B2 | 9/2006 | Ross et al. |
| 7,136,693 B2 | 11/2006 | Brodnick |
| 7,153,262 B2 | 12/2006 | Stivoric et al. |
| 7,162,294 B2 | 1/2007 | Rowlandson et al. |
| 7,171,166 B2 | 1/2007 | Ng et al. |
| 7,188,151 B2 | 3/2007 | Kumar et al. |
| 7,215,991 B2 | 5/2007 | Besson et al. |
| 7,222,054 B2 | 5/2007 | Geva |
| 7,236,818 B2 | 6/2007 | Mcleod et al. |
| 7,257,448 B2 | 8/2007 | Crowe et al. |
| 7,260,429 B2 | 8/2007 | Siejko et al. |
| 7,261,690 B2 | 8/2007 | Teller et al. |
| 7,285,090 B2 | 10/2007 | Stivoric et al. |
| 7,319,425 B2 | 1/2008 | Fiorenza et al. |
| 7,324,836 B2 | 1/2008 | Steenstra et al. |
| RE40,116 E | 2/2008 | Engstrom |
| 7,349,574 B1 | 3/2008 | Sodini et al. |
| 7,351,207 B2 | 4/2008 | Priemer |
| 7,354,400 B2 | 4/2008 | Asafusa et al. |
| 7,383,297 B1 | 6/2008 | Atsmon et al. |
| 7,415,304 B2 | 8/2008 | Rowlandson et al. |
| 7,444,116 B2 | 10/2008 | Ivanov et al. |
| 7,509,159 B2 | 3/2009 | Xue et al. |
| 7,520,860 B2 | 4/2009 | Guion-Johnson et al. |
| 7,542,878 B2 | 6/2009 | Nanikashvili |
| 7,548,623 B2 | 6/2009 | Manabe |
| 7,552,081 B2 | 6/2009 | Dutta et al. |
| 7,596,405 B2 | 9/2009 | Kurzweil et al. |
| 7,603,148 B2 | 10/2009 | Michalak |
| 7,654,148 B2 | 2/2010 | Tomlinson, Jr. et al. |
| 7,657,479 B2 | 2/2010 | Henley |
| 7,668,589 B2 | 2/2010 | Bauer |
| 7,689,437 B1 | 3/2010 | Teller et al. |
| 7,701,895 B2 | 4/2010 | Gehasie et al. |
| 7,733,224 B2 | 6/2010 | Tran |
| 7,742,808 B2 | 6/2010 | Nissilä |
| 7,819,814 B2 | 10/2010 | Gavriely et al. |
| 7,846,104 B2 | 12/2010 | Macquarrie et al. |
| 7,846,106 B2 | 12/2010 | Andrews et al. |
| 7,904,160 B2 | 3/2011 | Brodnick et al. |
| 7,945,064 B2 | 5/2011 | O'Brien, Jr. et al. |
| 7,945,462 B1 | 5/2011 | Goral |
| 7,946,959 B2 | 5/2011 | Shum et al. |
| 7,955,273 B2 | 6/2011 | Rahe-Meyer |
| 7,983,749 B2 | 7/2011 | Warren |
| 8,019,609 B2 | 9/2011 | Tamir et al. |
| 8,034,006 B2 | 10/2011 | Celik-Butler et al. |
| 8,062,090 B2 | 11/2011 | Atsmon et al. |
| 8,073,707 B2 | 12/2011 | Teller et al. |
| 8,078,136 B2 | 12/2011 | Atsmon et al. |
| 8,078,278 B2 | 12/2011 | Penner |
| 8,109,874 B2 | 2/2012 | Kong et al. |
| 8,126,566 B2 | 2/2012 | Stahmann et al. |
| 8,126,728 B2 | 2/2012 | Dicks et al. |
| 8,130,093 B2 | 3/2012 | Mazar et al. |
| 8,150,750 B2 | 4/2012 | Ray |
| 8,160,276 B2 | 4/2012 | Liao et al. |
| 8,165,677 B2 | 4/2012 | Von Arx et al. |
| 8,224,429 B2 | 7/2012 | Prstojevich et al. |
| 8,265,907 B2 | 9/2012 | Nanikashvili et al. |
| 8,275,635 B2 | 9/2012 | Stivoric et al. |
| 8,282,550 B2 | 10/2012 | Rasdal et al. |
| 8,285,356 B2 | 10/2012 | Bly et al. |
| 8,301,232 B2 | 10/2012 | Albert et al. |
| 8,301,236 B2 * | 10/2012 | Baumann et al. ............ 600/523 |
| 8,315,695 B2 | 11/2012 | Sebelius et al. |
| 8,323,188 B2 | 12/2012 | Tran |
| 8,328,718 B2 | 12/2012 | Tran |
| 8,332,233 B2 | 12/2012 | Ott et al. |
| 8,364,250 B2 | 1/2013 | Moon et al. |
| 8,369,936 B2 | 2/2013 | Farringdon et al. |
| 8,374,688 B2 | 2/2013 | Libbus et al. |
| 8,449,471 B2 | 5/2013 | Tran |
| 8,500,636 B2 | 8/2013 | Tran |
| 8,509,882 B2 | 8/2013 | Albert et al. |
| 8,519,835 B2 | 8/2013 | Dunko |
| 8,525,673 B2 | 9/2013 | Tran |
| 8,543,185 B2 | 9/2013 | Yuen et al. |
| 8,543,351 B2 | 9/2013 | Yuen et al. |
| 8,547,248 B2 | 10/2013 | Zdeblick et al. |
| 8,548,770 B2 | 10/2013 | Yuen et al. |
| 8,583,402 B2 | 11/2013 | Yuen et al. |
| 8,632,465 B1 * | 1/2014 | Brockway ............ 600/300 |
| 8,684,900 B2 | 4/2014 | Tran |
| 8,688,202 B2 * | 4/2014 | Brockway et al. ............ 600/515 |
| 8,700,137 B2 | 4/2014 | Albert |
| 2001/0025139 A1 * | 9/2001 | Pearlman ............ 600/301 |
| 2001/0027384 A1 | 10/2001 | Schulze et al. |
| 2001/0031998 A1 | 10/2001 | Nelson et al. |
| 2001/0051766 A1 | 12/2001 | Gazdzinski |
| 2002/0016541 A1 | 2/2002 | Glossop |
| 2002/0032386 A1 | 3/2002 | Sackner et al. |
| 2002/0065758 A1 | 5/2002 | Henley |
| 2002/0082665 A1 | 6/2002 | Haller et al. |
| 2002/0111556 A1 | 8/2002 | Wegner |
| 2002/0143576 A1 | 10/2002 | Nolvak et al. |
| 2003/0004425 A1 | 1/2003 | Narimatsu et al. |
| 2003/0093002 A1 | 5/2003 | Kuo |
| 2003/0097153 A1 * | 5/2003 | Bardy et al. ............ 607/5 |
| 2003/0107487 A1 | 6/2003 | Korman et al. |
| 2003/0117987 A1 | 6/2003 | Brebner |
| 2003/0149344 A1 | 8/2003 | Nizan |
| 2003/0193839 A1 | 10/2003 | Singh |
| 2004/0002662 A1 | 1/2004 | Hjelt et al. |
| 2004/0010201 A1 * | 1/2004 | Korzinov et al. ............ 600/518 |
| 2004/0034284 A1 | 2/2004 | Aversano et al. |
| 2004/0044292 A1 | 3/2004 | Yasushi et al. |
| 2004/0059205 A1 | 3/2004 | Carlson et al. |
| 2004/0093331 A1 | 5/2004 | Garner et al. |

(56) References Cited

U.S. PATENT DOCUMENTS

| | | |
|---|---|---|
| 2004/0117212 A1 | 6/2004 | Kong et al. |
| 2004/0143403 A1 | 7/2004 | Brandon et al. |
| 2004/0215088 A1 | 10/2004 | Hubelbank |
| 2004/0215094 A1 | 10/2004 | Baumer et al. |
| 2004/0220487 A1 | 11/2004 | Vyshedskiy et al. |
| 2004/0220488 A1 | 11/2004 | Vyshedskiy et al. |
| 2004/0225199 A1 | 11/2004 | Evanyk et al. |
| 2004/0228217 A1* | 11/2004 | Szeto .................. 368/11 |
| 2004/0236379 A1* | 11/2004 | Bardy et al. ............ 607/9 |
| 2004/0236819 A1 | 11/2004 | Anati et al. |
| 2004/0266407 A1 | 12/2004 | Lee et al. |
| 2004/0266480 A1 | 12/2004 | Hjelt et al. |
| 2005/0014531 A1 | 1/2005 | Findikli |
| 2005/0027207 A1 | 2/2005 | Westbrook et al. |
| 2005/0078533 A1 | 4/2005 | Vyshedskiy et al. |
| 2005/0124864 A1 | 6/2005 | Mack et al. |
| 2005/0234353 A1 | 10/2005 | Xue et al. |
| 2005/0267377 A1* | 12/2005 | Marossero et al. ........ 600/511 |
| 2006/0022833 A1 | 2/2006 | Ferguson et al. |
| 2006/0047215 A1 | 3/2006 | Newman et al. |
| 2006/0136744 A1* | 6/2006 | Lange .................. 713/186 |
| 2006/0173259 A1 | 8/2006 | Flaherty et al. |
| 2006/0190045 A1 | 8/2006 | Marcus et al. |
| 2006/0224051 A1 | 10/2006 | Teller et al. |
| 2006/0252999 A1 | 11/2006 | Devaul et al. |
| 2007/0021677 A1 | 1/2007 | Markel |
| 2007/0027386 A1 | 2/2007 | Such et al. |
| 2007/0032731 A1 | 2/2007 | Lovejoy et al. |
| 2007/0032733 A1* | 2/2007 | Burton ................. 600/509 |
| 2007/0063850 A1 | 3/2007 | Devaul et al. |
| 2007/0106179 A1 | 5/2007 | Bagha et al. |
| 2007/0156060 A1 | 7/2007 | Cervantes |
| 2007/0254604 A1 | 11/2007 | Kim |
| 2007/0265038 A1 | 11/2007 | Kim |
| 2008/0009759 A1 | 1/2008 | Chetham |
| 2008/0058670 A1 | 3/2008 | Mainini |
| 2008/0097537 A1* | 4/2008 | Duann et al. ............ 607/14 |
| 2008/0112885 A1 | 5/2008 | Okunev et al. |
| 2008/0114259 A1* | 5/2008 | Dal Molin et al. ........ 600/523 |
| 2008/0146890 A1 | 6/2008 | LeBoeuf et al. |
| 2008/0171945 A1 | 7/2008 | Dotter |
| 2008/0177162 A1 | 7/2008 | Bae et al. |
| 2008/0183093 A1* | 7/2008 | Duann et al. ............ 600/516 |
| 2008/0198872 A1 | 8/2008 | Pierce |
| 2008/0214903 A1 | 9/2008 | Orbach |
| 2008/0221632 A1* | 9/2008 | Bardy et al. ............ 607/5 |
| 2008/0228045 A1 | 9/2008 | Gao et al. |
| 2008/0293453 A1 | 11/2008 | Atlas et al. |
| 2009/0010461 A1 | 1/2009 | Klinghult et al. |
| 2009/0024045 A1 | 1/2009 | Prakash et al. |
| 2009/0037575 A1 | 2/2009 | Crystal et al. |
| 2009/0117883 A1 | 5/2009 | Coffing et al. |
| 2009/0144080 A1 | 6/2009 | Gray et al. |
| 2009/0149767 A1 | 6/2009 | Rossetti |
| 2009/0156908 A1 | 6/2009 | Belalcazar et al. |
| 2009/0171170 A1 | 7/2009 | Li et al. |
| 2009/0209873 A1 | 8/2009 | Pinter et al. |
| 2009/0273467 A1 | 11/2009 | Elixmann et al. |
| 2009/0279389 A1 | 11/2009 | Irie |
| 2009/0287067 A1 | 11/2009 | Dorogusker et al. |
| 2009/0312655 A1 | 12/2009 | Lo |
| 2010/0027379 A1 | 2/2010 | Saulnier et al. |
| 2010/0033303 A1 | 2/2010 | Dugan et al. |
| 2010/0042008 A1 | 2/2010 | Amitai et al. |
| 2010/0049006 A1 | 2/2010 | Magar et al. |
| 2010/0049037 A1 | 2/2010 | Pinter et al. |
| 2010/0063381 A1 | 3/2010 | Greiser |
| 2010/0069735 A1 | 3/2010 | Berkner |
| 2010/0076276 A1 | 3/2010 | Gilland |
| 2010/0094152 A1 | 4/2010 | Semmlow |
| 2010/0113950 A1 | 5/2010 | Lin et al. |
| 2010/0148956 A1 | 6/2010 | Song et al. |
| 2010/0152598 A1* | 6/2010 | Zhang .................. 600/515 |
| 2010/0184479 A1 | 7/2010 | Griffin, Jr. |
| 2010/0204758 A1 | 8/2010 | Boon et al. |
| 2010/0208434 A1 | 8/2010 | Kim et al. |
| 2010/0217099 A1 | 8/2010 | LeBoeuf et al. |
| 2010/0217100 A1 | 8/2010 | LeBoeuf et al. |
| 2010/0217144 A1* | 8/2010 | Brian ................... 600/523 |
| 2010/0217345 A1 | 8/2010 | Wolfe et al. |
| 2010/0256509 A1 | 10/2010 | Kuo et al. |
| 2010/0256699 A1* | 10/2010 | Makdissi ............... 607/5 |
| 2010/0281261 A1 | 11/2010 | Razzell |
| 2010/0298711 A1 | 11/2010 | Pedersen et al. |
| 2010/0324378 A1 | 12/2010 | Tran et al. |
| 2010/0331631 A1 | 12/2010 | Maclaughlin |
| 2011/0004110 A1* | 1/2011 | Shusterman ............ 600/509 |
| 2011/0015496 A1 | 1/2011 | Sherman et al. |
| 2011/0035927 A1 | 2/2011 | Griffin et al. |
| 2011/0066042 A1 | 3/2011 | Pandia et al. |
| 2011/0117529 A1 | 5/2011 | Barash et al. |
| 2011/0134725 A1 | 6/2011 | Su et al. |
| 2011/0152957 A1* | 6/2011 | Shaquer ................ 607/5 |
| 2011/0160601 A1 | 6/2011 | Wang et al. |
| 2011/0235466 A1 | 9/2011 | Booij et al. |
| 2011/0301439 A1 | 12/2011 | Albert et al. |
| 2011/0319949 A1* | 12/2011 | Bardy et al. ............ 607/7 |
| 2012/0051187 A1 | 3/2012 | Paulson |
| 2012/0053424 A1 | 3/2012 | Kenalty et al. |
| 2012/0071734 A1 | 3/2012 | Shimuta et al. |
| 2012/0116240 A1 | 5/2012 | Chou |
| 2012/0123232 A1* | 5/2012 | Najarian et al. .......... 600/345 |
| 2012/0123285 A1* | 5/2012 | Zhang ................... 600/516 |
| 2012/0123891 A1 | 5/2012 | Patel |
| 2012/0127833 A1 | 5/2012 | Ghen et al. |
| 2012/0136264 A1* | 5/2012 | Zhang ................... 600/515 |
| 2012/0143018 A1 | 6/2012 | Skidmore et al. |
| 2012/0147921 A1 | 6/2012 | Conti et al. |
| 2012/0157019 A1 | 6/2012 | Li |
| 2012/0157802 A1 | 6/2012 | Chou |
| 2012/0158090 A1 | 6/2012 | Chavan et al. |
| 2012/0171963 A1 | 7/2012 | Tsfaty |
| 2012/0179056 A1 | 7/2012 | Moulder et al. |
| 2012/0203124 A1 | 8/2012 | Lim |
| 2012/0221476 A1 | 8/2012 | Candelario |
| 2012/0316413 A1 | 12/2012 | Liu et al. |
| 2013/0030259 A1 | 1/2013 | Thomsen et al. |
| 2013/0046162 A1 | 2/2013 | Baumann et al. |
| 2013/0085364 A1 | 4/2013 | Lu et al. |
| 2013/0131530 A1* | 5/2013 | Brockway et al. ........ 600/513 |
| 2013/0197320 A1 | 8/2013 | Albert et al. |
| 2013/0236980 A1 | 9/2013 | Moretti et al. |
| 2013/0261414 A1 | 10/2013 | Tal et al. |
| 2013/0289424 A1* | 10/2013 | Brockway et al. ........ 600/509 |
| 2013/0331663 A1 | 12/2013 | Albert et al. |
| 2013/0338460 A1 | 12/2013 | He et al. |
| 2014/0050321 A1 | 2/2014 | Albert et al. |
| 2014/0222097 A1* | 8/2014 | Bardy et al. ............ 607/7 |
| 2014/0276162 A1 | 9/2014 | Albert et al. |
| 2015/0018702 A1 | 1/2015 | Galloway et al. |

FOREIGN PATENT DOCUMENTS

| | | |
|---|---|---|
| CN | 201918016 U | 8/2011 |
| CN | 102347804 A | 2/2012 |
| DE | 2506936 A | 9/1976 |
| DE | 4212670 A1 | 1/1994 |
| EP | 631226 A1 | 12/1994 |
| EP | 0980227 A1 | 2/2000 |
| EP | 1407713 A1 | 4/2004 |
| EP | 1782229 A | 5/2007 |
| EP | 1181888 B1 | 9/2007 |
| EP | 1238633 B1 | 10/2008 |
| EP | 2030565 A1 | 3/2009 |
| EP | 2116183 B1 | 2/2012 |
| FR | 2740426 A1 | 4/1997 |
| GB | 2181554 A | 4/1987 |
| GB | 2408105 A | 5/2005 |
| JP | 59-122032 A | 7/1984 |
| JP | 59-190742 A | 10/1984 |
| JP | 63-072231 A | 4/1988 |
| JP | 63-294044 A | 11/1988 |
| JP | 1-244328 A | 9/1989 |
| JP | 5-167540 A | 7/1993 |

(56) References Cited

FOREIGN PATENT DOCUMENTS

| | | |
|---|---|---|
| JP | 6-326669 A | 11/1994 |
| JP | 2002191562 A | 7/2002 |
| JP | 2002-261731 A | 9/2002 |
| JP | 2003-010177 A | 1/2003 |
| JP | 2005-295378 A | 10/2005 |
| JP | 2012-065073 A | 3/2012 |
| MX | 2009011781 A1 | 5/2011 |
| WO | WO 82/00910 A1 | 3/1982 |
| WO | WO 88/05282 A1 | 7/1988 |
| WO | WO 90/08361 A1 | 7/1990 |
| WO | WO 92/06551 A1 | 4/1992 |
| WO | WO 97/31437 A1 | 8/1997 |
| WO | WO98/38611 A1 | 9/1998 |
| WO | WO-9838909 A1 | 9/1998 |
| WO | WO-9858338 A2 | 12/1998 |
| WO | WO-9904043 A1 | 1/1999 |
| WO | WO99/44494 A1 | 9/1999 |
| WO | WO00/41620 A1 | 7/2000 |
| WO | WO01/47597 A2 | 7/2001 |
| WO | WO 01/57619 A2 | 8/2001 |
| WO | WO-0233846 A1 | 4/2002 |
| WO | WO02/080762 A1 | 10/2002 |
| WO | WO03/075118 A2 | 9/2003 |
| WO | WO03/094720 A1 | 11/2003 |
| WO | WO2004/037080 A1 | 5/2004 |
| WO | WO-2005124864 A1 | 12/2005 |
| WO | WO2006/001005 A2 | 1/2006 |
| WO | WO-2006021956 A2 | 3/2006 |
| WO | WO2007/014545 A2 | 2/2007 |
| WO | WO2007/088315 A1 | 8/2007 |
| WO | WO2008/005015 A1 | 1/2008 |
| WO | WO 2008/066682 A2 | 6/2008 |
| WO | WO2010/025166 A1 | 3/2010 |
| WO | WO2010/108287 A1 | 9/2010 |
| WO | WO2010/113354 | 10/2010 |
| WO | WO 2010/144626 A1 | 12/2010 |
| WO | WO 2011/006356 A1 | 1/2011 |
| WO | WO 2011/008838 A1 | 1/2011 |
| WO | WO 2011/014292 A1 | 2/2011 |
| WO | WO 2011/022942 A1 | 3/2011 |
| WO | WO 2011/040877 A1 | 4/2011 |
| WO | WO2011/040878 A1 | 4/2011 |
| WO | WO2011/113070 A1 | 9/2011 |
| WO | WO 2011/137375 A2 | 11/2011 |
| WO | WO2012/046158 A1 | 4/2012 |
| WO | WO2012/108895 A1 | 8/2012 |
| WO | WO2012/129413 A1 | 9/2012 |
| WO | WO2012/160550 A1 | 11/2012 |
| WO | WO2013/036307 A1 | 3/2013 |
| WO | WO2013/066642 A1 | 5/2013 |
| WO | WO2013/093690 A1 | 6/2013 |
| WO | WO2013/122788 A1 | 8/2013 |
| WO | WO2013/138500 A1 | 9/2013 |
| WO | WO2013/155196 A2 | 10/2013 |
| WO | WO2013/192166 A1 | 12/2013 |

OTHER PUBLICATIONS

Adidas miCoach Pacer Review: Like Nike+, Only Better; printed from website http://gizmodo.com/5479456/adidas on Mar. 4, 2010; 5 pgs.

Australian Design Awards; Heartplus Micro; printed from website http://www.designawards.com/au on Apr. 12, 2002; 6 pgs.

Bajaj, M.D.; Event Recording in Ambulatory Patients with Syncopal Events; University of Kansas; Wichita, Kansas; (no date); pp. 15-18; printed on or before Apr. 14, 2010.

Bluetooth; Headset Profile (HSP); printed from website http://bluetooth.com/English/Technology/Works/Pates/HSP.aspx, printed May 12, 2010; 1 pg.

Bramanti et al., Multichannel telemetric system for biomedical signals via switched telephone lines; Medical and Biological Engineering and Computing, Sep. 1982, vol. 20, No. 5, pp. 653-656.

Burke, A Micropower Dry-Electrode ECG Preamplifier; IEEE Transactions on Biomedical Engineering, Feb. 2000, vol. 47, No. 2, pp. 155-162.

Card Guard; CG-6108 ACT Ambulatory Cardiac Telemetry Brochure; Card Guard, The Telemedicine Company: Switzerland; (year of publication is sufficiently earlier than the effective U.S. filing date and any foreign priority date) 2006; 2 pgs.

Cardiocomm Solutions; GEMS Air (PC based ECG management); printed from website http://www.cardiocommsolutions/com on Mar. 19, 2010; 1 pg.

Charuvastra; Transtelephonic Cardiac Event Recording for Arrhythmia Surveillance; printed from website http://tchin.org/resource_room/c_art on Mar. 26, 2010; 2 pgs.

Cheng, Allen C.; Real-Time Cardiovascular Diseases Detection on a Smartphone; printed Apr. 14, 2010.

Company-Bosch et al.; ECG Front-End Design is Simplified with MicroConverter; Analog Dialogue; Nov. 2003; vol. 37(11); pp. 1-5.

Creative; PC-80B Portable ECG Monitor w/sd card extension slot; printed from website www.amazon.com/Portable-Monitor-extension-leather-shipping/dp/B001OjWKUE on Feb. 4, 2010; 3 pgs.

Deveau, Health care eyes smart phones to heal ills (posted Sep. 15, 2009); printed from website http://www.theQiobeandmail.com on Sep. 17, 2009, 4 pages.

Dinh; Heart Activity Monitoring on Smartphone; IPCBEE-Int Conf Biomedical Eng and Technol; 11:45-49; Jun. 17-19, 2011.

Dobrev, et al.; Bootstrapped two-electrode biosignal amplifier; Med Biol Eng Comput; vol. 46(6); Jun. 2008, pp. 613-619.

Elert, Glenn (Editor); Frequency Range of Human Hearing; The Physics Factbook; web version as of Mar. 29, 2010; 2 pgs.; printed Jun. 6, 2012 (http://web.archive.org/web/20100329141847/http://hypertextbook.com/facts/2003/ChrisDAmbrose.shtml).

Favorite Plus; Handheld Easy ECG Monitor; (Product ID: FP180); printed from website www. favoriteplus.com/easy-ecg-handheld-monitor-fp180 on Feb. 4, 2010; 2 pgs.

Favorite Plus; Handheld ECG Monitor—Handheld EKG Monitor at Favoriteplus.com (Products: FP180, FP-RMH and FP-ICH); printed from website www.favoriteplus.com/handheld-ecg-ekg-monitor.php on Feb. 4, 2010; 3 pgs.

Favorite Plus; Handheld EKG Monitor InstantCheck; (Product ID: FP-ICH); printed from website http://www. favoriteplus.com/instanchcheck-hand held-ecg-ekg-monitor on Feb. 4, 2010; 2 pgs.

Ferrick, M.D., Holter Monitoring and Cardiac Event Recording in Assessing Symptomatic Patients; Albert Einstein College of Medicine; Bronx, New York; (no date); pp. 11-14; printed on or before Apr. 14, 2010.

Fulford-Jones, et al., A Portable, Low-Power, Wireless Two-Lead EKG System; Proc. of the 26th Ann. Int. Conf. IEEE EMBS; San Francisco, CA, USA; Sep. 1-5, 2004, pp. 2141-2144.

Gillette, M.D.; Diagnosis of Pediatric Arrhythmias with Event Recording; Medical University of South Carolina; Charleston, South Carolina; (no date); pp. 25-32; printed on or before Apr. 14, 2010.

Grier, James W.; How to use 1-lead ECG recorders to obtain 12-lead resting ECGs and exercise ("stress") ECGs; printed from website http://www.ndsu.edu/pubweb/grier on Jun. 7, 2010; 13 pgs.

Hannaford, Kat; How to Turn Your iPhone into a Laser, Fan or Flashlight; printed from website http://m.gizmodo.com/5534904; printed Feb. 3, 2011.

Hayes, M.D., Approaches to Diagnosing Transient Arrhythmias—An Overview; Mayo Clinic; Rochester, Minnesota; (no date); pp. 7-10; printed on or before Apr. 14, 2010.

Hearing Loss Assoc. of Kentuckiana; Decibal Ratings/Hazardous Time Exposures of Common Noise (excerpt from Survivor's Manual); web version as of Oct. 5, 2008; 2 pgs.; printed Jun. 6, 2012 (http://web.archive.org/web/20081005143856/http://www.hearinglossky.org/hlasurvival1.html).

Huang, Tina; Age-related hearing loss; Minnesota Medicine; 90(10); pp. 48-50; Oct. 2007; printed Jun. 6, 2012 from: http://www.minnesotamedicine.com/PastIssues/PastIssues2007/October2007/ClincalHuangOctober2007.aspx).

IMEC News; IMEC extends flexible ECG patch to enable arrhythmia detection; printed from website http://www2.imec.be/imec on Aug. 18, 2009; 1 pg.

(56) References Cited

OTHER PUBLICATIONS

Instromedix; Cardiac Event Recording FAQs; Instromedix: A Card Guard Company, San Diego, CA; printed from website www.instromedix.com/pdf/products/cardiac; printed on or before Apr. 14, 2010.
Instromedix; The Arrhythmia Monitoring System; King of Hearts Express AF Recorder Brochure; from Instromedix; A CardGuard Company; Rosemont IL; (year of publication is sufficiently earlier than the effective U.S. filing date and any foreign priority date) 2004; 3 pgs.
iRHYTHM; Zio(TM) Patch; printed from website http://www.irhythmtech.com/zio-solution/zio-pach/, printed Apr. 12, 2010.
Jenkins II, W.; Time/Frequency Relationships for an FFT-Based Acoustic Modem; Naval Postgraduate School; pp. 1-102; Sep. 2010 (http://edocs.nps.edu/npspubs/scholarly/theses/2010/Sep/10Sep_Jenkins.pdf) printed Oct. 2, 2013.
Kim, et al., Detection of Atrial Fibrillation Episodes using Multiple Heart Rate Variability Features in Different Time Periods; Conf Proc IEEE Eng Med Biol Soc.; EMBS; 30th Ann. Int. Conf.; Aug. 20-25, 2008, 5482-5485.
Koerner; The Author's Metrics; Wired Magazine Article; New York, NY; Jul. 2009; pp. 93-126.
Kumparak, Greg; Visa officially announces their case that turns your iPhone into a credit card (and we've got pics!); May 17, 2010; www.mobilecrunch.com; printed Feb. 3, 2011.
Leijdekkers et al., Trial Results of a Novel Cardiac Rhythm Management System using Smart Phones and Wireless ECG Sensors; Proc. of the 7th Int. Conf. on Smart homes and health Telematics., Tours, France; Jul. 1-3, 2009; 8 pgs.
Levkov et al., Removal of power-line interference from the ECG: a review of the subtraction procedure; BioMedical Engineering Online; 4:50; Aug. 23, 2005; 18 pgs.; (printed from website http://www.biomedical-engineeringonline.com/content/4/1/50).
M Med Choice; (company information page) Beijing Choice Electronic Technology Co., Ltd.; printed from website http://www.choicemmed.com/1xwm .asp; printed Dec. 28, 2009; 1 page.
M Med Choice; Handheld ECG Monitor Brochure; MD100 Products; Beijing Choice Electronic Technology Co. Ltd.; 6 pgs; published on or before Apr. 14, 2010.
M Med Choice; Handheld ECG Monitor MD100A1; printed from website http://www.choicemmed.com/productshow.asp on Dec. 28, 2009; 2 pgs.
M Med Choice; Handheld ECG Monitor MD100B; printed from website http://www.choicemmed.com/productshow.asp on Dec. 28, 2009; 2 pgs.
Mauvila: Mauvila ECG Tutorial; Basic ECG Interpretation Tutorial; Sections 1-12; 2004; printed from website http://mauvila.com/ECG/ecg.htm on Mar. 26, 2010; 57 pgs.
Medgadget; Zio(TM) Patch Wins Medical Design Award; MedGadget internet journal of emerging medical technologies; printed from website http://medgadget.com/archives/2010/04/zio patch wins medial desian award 1.html on Apr. 12, 2010; 1 pg.
MiCardioMobile: Remote Wireless Cardiac Rehabilitation Monitoring printed from website; http://alivetec.cable.nu/cardiomobile; 1 page; printed Apr. 14, 2010.
Mobility Mind; Use your Treo 650 as a portable ECG monitoring device; Mobility Mind; Sep. 14, 2005, printed from website http://www.treotoday.net/2005/09/14/use-your-treo-650-as-a-portable-ecg-monitoring-device/ (accessed Mar. 26, 2010); 1 pg.
Modem Protocols Explained; ftp://kermit.columbia.edu/kermit/cu/protocol.html; 5 pgs.; printed Oct. 2, 2013.
Modem Tutorial; http://www.lsu.edu/OCS/its/unix/tutorial/ModemTutorial/ModemTutorial.html; 2 pgs.; printed Oct. 2, 2013.
Muench, Frederick PhD; HRV: The Manufacturers and Vendors Speak; The portable StressEraser Heart Rate Variability Biofeedback Device: Background and Research; Biofeedback; vol. 36, Iss. 1; pp. 35-39; Spring 2008.
Murph; RedEye mini converts iPhone, iPad or iPod touch into IR-beaming universal remote; printed from website http://www.engadget.com/2010/03/02/redeye on Mar. 2, 2010; 2 pgs.
Nam et al.; An Ultrasonic Sensor Based Low-Power Acoustic Modem for Underwater Communication in Underwater Wireless Sensor Networks; Computer Network Lab, Dept. of Elec. Eng., Korea Univ.; pp. 494-504; Dec. 2007 (http://nesl.ee.ucla.edu/fw/torres/home/Dropbox/good_paper_mico_controller.pdf; 11 pgs.; printed Oct. 2, 2013).
Neuroreille; Audiometry; web version as of Oct. 14, 2008; 1 pg.; printed Jun. 6, 2012 (http://www.neuroreille.com/promenade/english/audiometry/audiometry.htm).
Omron; Omron Portable ECG EKG Handheld HCG-801 Monitor; printed from website http://www.amazon.com/Omron-Portable-Handheld-HCG-801-Monitor/dp/B0019WH3EO on Feb. 24, 2010; 4 pgs.
Omron; Omron Portable ECG Monitor; printed from website http://www.target.com/gp/detail.html on Mar. 26, 2010; 1 pg.
Oresko, et al., Detecting Cardiovascular Diseases via Real-Time Electrocardiogram Processing on a Smartphone; 2009 Workshop on Biomedicine in Computing: Systems, Architectures, and Circuits (BiC); Austin, TX; Jun. 2009; pp. 13-16.
Perez, Sarah; No NFC? No Problem; New Startup Zoosh Provides Workaround Technology (Jun. 20, 2011); printed on or before Jun. 27, 2011 from website; 2 pgs.; (http://www.readwriteweb.com/archives).
Prystowsky, M.D., Chairmans Introduction; Duke University Medical Center; Indianapolis, Indiana; pp. 5-6; printed on or before Apr. 14, 2010.
Prystowsky, M.D., Chairmans Summary; Duke University Medical Center; Indianapolis Indiana; (no date); pp. 39-40; printed on or before Apr. 14, 2010.
Prystowsky, M.D., The Clinical Application, Diagnostic Yield and Cost Considerations of Cardiac Event Recorders; Duke University Medical Center; Indianapolis Indiana; (no date); pp. 19-23• printed on or before Apr. 14, 2010.
Puurtinen, et al., Best Electrode Locations for a Small Bipolar ECG Device: Signal Strength Analysis of Clinical Data, Annals of Biomedical Engineering, vol. 37, No. 2, Feb. 2009; pp. 331-336.
Raju; Heart-Rate and EKG Monitor Using the MSP430FG439 (Application Report); Texas Instruments; SLAA280—Oct. 2005—(Revised Sep. 2007); 11 pgs.
Read-My-Heart; ECG Machine Handheld Read My Heart; (Product Item No. HH-3413); printed from website http://www.helioliving.com/ECG-Machine-Handheld-ReadMyHeart on Feb. 4, 2010; 1 pg.
Read-My-Heart; ReadMyHeart Personal Handheld ECG Monitor with Free Illustrator Book & Free Electrodes V2.2; printed from website http://www .amazon.com/Readmyheart-Personai-Handheld-illustrator-Electrodes/dp/B0010AN63W on Mar. 26, 2010; 1 pg.
Ricker; Square payment dongle demoed for iPhone toting hippies and you (video); printed from website http://www.engadget.com/2010/01/18/square-payment on Jan. 18, 2010; 6 pgs.
Rockwood; Interviews: The Networked Body Magazine Article from Fast Talk Magazine; Jul. 2009; pp. 19-26.
Salahuddin, et al., Ultra Short Term Analysis of Heart Rate Variability using Normal Sinus Rhythm and Atrial Fibrillation ECG Data; e-Health Networking, App. and Services; 9th Int. Conf.; IEEE; Taipei, TW; pp. 240-243; Jun. 19-22, 2007.
Semler, M.D.; The Future of Cardiac Event Monitoring; St. Vincent Hospital and Medical Center; Portland, Oregon; (no date); pp. 33-37; printed on or before Apr. 14, 2010.
SFO Medical; Choice Portable Handheld ECG EKG Monitor; printed from website http://www.amazon.com/Choice-Portable-Handheld-ECG-Monitor/dp/B001Q74VOM on Mar. 26, 2010; 1 page.
Shenzen New Element Med. Equipment; Wireless ECG Monitoring System; printed from website http://www.alibaba.com/product-gs/248168581/Wireless ECG Monitoring system. html. On Mar. 26, 2010.
Shumaker, J.; Designing an Ultrasonic Modem for Robotic Communications; Army Research Laboratory; 26 pgs.; Mar. 2009 (http://www.dtic.mil/cgi-bin/GetTRDoc?AD=ADA499556) printed Oct. 2, 2013.
Smith; Smartphone may keep the cardiologist away; The Independent; Mar. 5, 2010; printed from website http://www.independent.co.

(56) References Cited

OTHER PUBLICATIONS uk/life-style/health-and-families/health-news/smartphone-may-keep-the-cardiologist-away-1916652.html on Mar. 26, 2010.
Stevens, Tim; Apple's Seamlessly Embedded Heart Rate Monitor could turn theiPhone into a new-age mood ring (posted May 6, 2010); printed from website www.engadget.com on May 6, 2010; 3 pgs.
Taleb Medical; Observer Hand-held ECG Monitor MD100B; printed on or before Apr. 14, 2010.
Tei, et al., New index of combined systolic and diastolic myocardial performance: a simple and reproducible measure of cardiac function—a study in normals and dilated cardiomyopathy; J Cardiol.; 26(6):357-366; Dec. 1995.
Texas Instruments; Information for Medical Applications, Biophysical Monitoring—Electrocardiogram (ECG) Front End; Apr. 2004, pp. 17-18.
Tschida (posted by); Power A's New Case Turns Your iPhone Into a Universal Remote; printed from website http://appadvice.com/appnn on Mar. 1, 2010; 2 pgs.
Vanhemert, Kyle; XWave Headset Lets You Control iPhone Apps With Your Brain; Sep. 8, 2010; printed from website http://gizmodo.com; printed Sep. 8, 2010.
Free2move; Vitaphone 2300; www.free2move.us/News/NewsVitaphone 240105.htm; printed May 12, 2010; 2 pgs.
Wikimedia Laboratories; Acoustics; web archive version dated Jan. 25, 2009; 2 pgs.; printed Jun. 6, 2012 (http://liveweb.archive.org/http://en.labs.wikimedia.org/wiki/Acoustics).
Wikipedia; Aliasing; web version as of Apr. 3, 2011; 5 pgs.; printed Jun. 6, 2012 (http://liveweb.archive.org/http://en.wikipedia.org/w/index.php?title=Aliasing&oldid=422141882).
Wikipedia; Hearing Range; web version as of Feb. 6, 2010; 5 pgs.; printed Jun. 6, 2012 (http://web.archive.org/web/20100206213741/http://en.wikipedia.org/wiki/Hearing_range).
Wikipedia; Pulse oximetry; printed from website httg://en.wikipedia.org on May 10, 2010, 4 pages.
Wisneski, C.; Ultrasonic Local Area Communication; http://alumni.media.mit.edu/~wiz/ultracom.html; 2 pgs.; printed Oct. 2, 2013.
Woodward et al.; Bio-Potential-to-Frequency Converter/Modulator; Electronic Design; Aug. 9, 1999; p. 117.
Ziegler, Chris; EPI Life phone sports ECG function, can let doctors know if you're not gonna make it; printed from website http://www.engadget.com/2010/06/16/epi-life-phonesports on Jun. 17, 2010; 4 pgs.
Albert et al.; U.S. Appl. No. 13/969,446 entitled "Ultrasonic Transmission of Signals," filed Aug. 16, 2013.
Albert, David E.; U.S. Appl. No. 14/015,303 entitled "Cardiac Performance Monitoring System for Use with Mobile Communications Devices," filed Aug. 30, 2013.
Dolan; Qualcomm launches ECG smartphone program in China; Sep. 8, 2011; 11 pgs.; retrieved Mar. 19, 2014 from the internet (http://mobihealthnews.com/13092/qualcomm-launches-ecg-smartphone-program-in-china/).
Garabelli et al. Accuracy and Novelty of an Inexpensive iPhone-based Event Recorder (Presentation Poster/Abstract) Heart Rhythm 2012, 33rd Annual Scientific Session. SP23. Innovation Poster Session II. No. IA02-1; May 11, 2012.
GBI Portal; Qualcomm's wireless reach mHealth project to improve cardiovascular disease in resource scarce China; Feb. 17, 2012; 7 pgs.; retrieved Mar. 19, 2014 from the internet (http://www.integrallc.com/2012/02/17/qualcomms-wireless-reach-mhealth-project-to-improve-cardiovascular-disease-in-resource-scarce-china/).
Lau et al. Validation of an iPhone ECG application suitable for community screening for silent atrial fibrillation—A novel way to prevent stroke (Presentation Abstract 16810); American Heart Association 2012 Scientific Sessions and Resuscitation Science Symposium; 126(1); Nov. 20, 2012.
Lowres, et al. Screening Education and Recognition in Community pHarmacies of Atrial Fibrillation to prevent stroke in an ambulant population aged >=65 years (Search-AF stroke prevention study): a cross-sectional study protocol. BMJ Open. Jun. 25, 2012; 2(3); pii: e001355. doi: 10.1136/bmjopen-2012-001355.
MacFarlane et al.; Resting 12-lead ECG electrode placement and associated problems; SCST Update 1995; 15 pgs.; printed Feb. 18, 2014 from www.scst.org.uk/resources/RESTING_12.pdf? (year of pub. sufficiently earlier than effective US filing date and any foreign priority date).
Saxon, et al. iPhone rhythm strip—the implications of wireless and ubiquitous heart rate monitoring. JACC; 59(13): E726; Mar. 2012.
Vitaphone; Telemedicine since 1999: Modern health management is our special subject; 3 pgs; retrieved Mar. 19, 2014 from the internet (http://www.vitaphone.de/en/company/history-of-vitaphone/).
Lau, et al. iPhone ECG application for community screening to detect silent atrial fibrillation: A novel technology to prevent stroke. Int J Cardiol. Apr. 30, 2013;165(1):193-4.
Lau, et al. Performance of an Automated iPhone ECG Algorithm to Diagnose Atrial Fibrillation in a Community AF Screening Program (Search-AF). Heart, Lung and Circulation. 2013; 22(1): S205; 2013 (Abstracts for the Cardiac Society of Australia and New Zealand Annual Scientific Meeting and the International Society for Heart Research Australasian Section Ann. Scientific Meeting, Aug. 8-11, 2013, Gold Coast).
Saxon. Ubiquitous Wireless ECG Recording: A Powerful Tool Physicians Should Embrace. J Cardiovasc Electrophysiol. 24(4): pp. 480-483; Apr. 2013.
Albert et al.; U.S. Appl. No. 14/149,242 entitled "Methods and systems for electrode placement," filed Jan. 7, 2014.
Albert et al.; U.S. Appl. No. 14/217,032 entitled "Systems and methods for processing and analyzing medical data," filed Mar. 17, 2014.
Company-Bosch et al.; ECG Front-End Design is Simplified with MicroConverter; Analog Dialogue; Nov. 2003; vol. 37(11); 12 pages.
Dolan. FDA promises regulatory guidance this year. Mobihealthnews. Mar. 17, 2011. (http://mobihealthnews.com/10495/fda-promises-regulatory-guidance-this-year/), 10 pages.
Dower, et al. Time-selective filtering for computerized electrocardiography. Computers in Cardiology. Sep. 1979; 267-270.
Fausti-Flora, et al. Data Critical's RhythmStat XL Technology Receives FDA Clearance Bringing a Revolutionary Wireless Solution to the Telemedicine Marketplace. Business Wire. Dec. 11, 1997, 5 pages.
Haberman et al., Wireless smart phone equipped ECG enables large scle screening in diverse populations. Unpublished abstract. 2 pages.
Hickey, et al. Detection of Recurrent Atrial Fibrillation Utilizing Novel Technology. Journal of Atrial Fibrillation. Dec. 2013-Jan. 2014; 6(4):50-52.
International search report and written opinion dated Feb. 24, 2014 for PCT/US2013/069290.
International search report dated Aug. 18, 2014 for PCT/US2014/030780.
Lowres et al., Feasibility and cost effectiveness of stroke prevention through community screening for atrial fibrillation using iPhone ECG in pharmacies. Thrombosis and Haemostasis, 111.6, 2014, 2 pages.
McManus et al., A novel application for the detection of an irregular pulse using an iPhone 4S in patients with atrial fibrillation. Heart Rhythm, 10:315-319 (2013).
OCHS. The Wello smartphone case puts health data in the palm of your hand. Mar. 6, 2014. TechHive blog. http://www.techhive.com/article/2105322/the-wello-smartphone-case-puts-health-data-in-the-palm-of-your-hand.html, 3 pages.
Office Action dated Apr. 7, 2015 for U.S. Appl. No. 14/217,032.
Rohan. How to Save Lives with CE: Data Critical Corp's RhythmStat XLS Interview with developers David Albert, MD and Landgrave Smith, Ph.D. 1999. (http://www.bitcave.com/savelive.pdf), 4 pages.
Telecompaper. Data Critical Launches Rhythmstat XL Medical System. Jan. 8, 1998. (http://www.telecompaper.com/news/data-critical-launches-rhythmstat-xl-medical-system--126725), 5 pages.
Wello by Azoi Inc. 2014. https://azoi.com (Product is now named KITO).

* cited by examiner

ELECTROCARDIOGRAM SIGNAL DETECTION

CROSS REFERENCE TO RELATED APPLICATIONS

This patent application claims priority to U.S. provisional patent application No. 61/723,788, filed Nov. 8, 2012, and titled "ATRIAL FIBRILLATION DETECTION", and U.S. provisional patent application No. 61/802,091, filed Mar. 15, 2013 and titled "ATRIAL FIBRILLATION DETECTION". The disclosures of these applications are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The devices, systems and methods described herein relate to electrocardiogram (ECG) monitoring and, more specifically, apparatuses (including systems and devices) and methods for processing an ECG signal to reduce noise in the signal and/or analyze the ECG signal(s), including detection of signals indicative of normal and abnormal (e.g., atrial fibrillation) heart beats.

BACKGROUND

The analysis of cardiac electrophysiological activity such as electrocardiograms (ECGs) increasingly informs the management of cardiac disorders and irregularities, such as atrial fibrillation. Skin surface ECG signal analysis is typically based on waveform time domain parameters, and may depend heavily on the quality of the signal received and analyzed. Thus, the higher quality of the recorded ECG, the more reliable the information that can be extracted from the recorded waveform. Such waveforms may be analyzed (typically after standard filtering and "cleaning" of the signal) for various indicators useful to detect cardiac events or status, such as cardiac arrhythmia detection and characterization. Indicators may include heart rate variability (HRV), cardiac wave morphology, R wave-ST segment and T wave amplitude analysis.

Recently, hand-held monitors have been developed that work with mobile telecommunications devices. For example, U.S. Pat. Nos. 8,509,882 and 8,301,232 to Albert describe hand-held ECG devices that may be used with mobile telecommunications devices. Because the accurate interpretation and analysis of ECG signals requires relies upon the quality of the signals received/recorded, techniques for cleaning up signals to remove artifacts has been proposed. Known cardiac monitoring systems that may include detection and characterization of cardiac markers many not be sufficiently robust to handle signals, particularly including signals taken with handheld ECG devices including those mentioned above, which may use dry electrodes that can be held against the patient's skin by the patient or medical professional, which may result in artifacts such as motion artifacts, environmental artifacts, and contact artifacts. Inaccurate and subjective evaluation and diagnosis may cause unexpected delay in cardiac rhythm management, drug delivery and emergency treatment.

In addition, existing apparatuses and methods for de-noising ECG signals are typically applied before interpreting an ECG signal. As mentioned, although it is beneficial to interpret signals that are as noise-less and representative of the actual electrical activity of the heart as possible, most apparatuses and methods for de-noising alter a putative ECG signal before it is analyzed for cardiac markers, possibly removing non-noise signal when removing artifactual components. Thus, in some variations it may be beneficial to at least partially interpret signals before and/or during de-noising procedures.

An example of an idealized version of a typical ECG waveform is shown in FIG. 9, illustrating multiple cycles. In general, ECG devices may include one, two, three, or more (e.g., six, twelve) leads. It would be helpful to provide robust ECG signal conditioning and analysis of any or all leads including 12-lead ECG and multi-channel intra-cardiac electrograms (ICEG) devices.

Furthermore, known waveform morphology parameter analysis systems, such as P wave, QRS complex, ST segment, T wave analysis systems, are used for cardiac arrhythmia monitoring and identification, e.g., of atrial fibrillation (AF), myocardial ischemia (MI) and ventricular tachycardia/fibrillation (VT/VF). However, known waveform morphology parameter analysis is often subjective and time-consuming, and requires extensive medical expertise and clinical experience for accurate interpretation and proper cardiac rhythm management.

Known clinical methods use electrophysiological (EP) surface ECG and ICEG signal voltage amplitude analysis for arrhythmia detection to identify and characterize cardiac abnormality and arrhythmia related information (such as timing, energy). Known clinical diagnosis standards may be of limited value in some cases. For example, myocardial ischemia and infarction detection is usually based on ST segment voltage deviation for ischemia event detection (e.g. 0.1 mV elevation). Known methods for cardiac arrhythmia analysis, such as myocardial ischemia event detection and evaluation, rely on a repolarization signal portion, such as ST segment and T wave morphology changes. Such methods lack capability for quantitative characterization of cardiac arrhythmia severity and may cause a false alarm. For example amplitude voltage ST segment measurement fails to provide a reliable severity level of an ischemia event. Heart rate variability is unable to provide an arrhythmia urgency level.

The apparatuses, including systems and devices, and methods implementing or operating them described herein may address the deficiencies and related problems discussed above.

SUMMARY OF THE DISCLOSURE

The present invention relates to apparatuses (devices and systems) and methods for extracting, de-noising, and analyzing electrocardiogram signals. Although the apparatuses and methods described herein may be used with, or as part of, any ECG system, including single-lead and multiple-lead systems, any of these apparatuses and methods described herein may be used with hand-held ECG devices including ECG devices for use with a mobile telecommunications device such as a smartphone.

In general, the term "apparatus" is used herein to include devices and systems. These may include hardware, software, firmware, or combinations thereof. Any of the apparatuses described may be implemented as part of an ECG system or in communication with an ECG system, which may include two or more pairs of electrodes. Any of the apparatuses described herein may be implemented as a (or as part of a) computerized system. In particular, any of the apparatuses described herein may include non-transitory computer-readable storage medium storing a set of instructions capable of being executed by a processor, that when executed by the processor, causes the processor to extract an electrocardiogram (ECG) signal by performing any or all of the steps described herein.

For example, described herein are apparatuses and methods of using them or performing the methods, for extracting and/or de-noising ECG signals from a starting signal. An extracted ECG signal typically includes an ECG signal that is isolated from the starting signal by removing artifacts (e.g., noise) as described herein. The starting signal may be a raw signal, such a signal received directly from a pair of ECG electrodes or received after processing. The starting signal may be pre-filtered, amplified, de-noised, or conditioned. The starting signal may be a combined signal combining multiple signals from a single lead or from multiple leads.

Also described herein are apparatuses and methods for analyzing an ECG signal, for example, to generate one or more indicators or markers of cardiac fitness, including in particular indicators of atrial fibrillation. These apparatuses and methods may include apparatuses configured (using software, hardware, firmware, and combinations of these) to determine or generate one or more indicator or markers during and/or after the process of extracting an ECG signals.

Thus, described herein are apparatuses and method for determining if a patient is experiencing a cardiac event, such as an arrhythmia. Any of the apparatuses and methods described herein may include a report (such as a signal, alarm, warning, communication, display, etc.) indicating the presence, absence, or likelihood of an arrhythmia based on the extracted ECG.

In any of the variations described herein, the apparatus and/or method may be configured to clean up (e.g., de-noise, remove artifact, etc.) an ECG signal from a starting signal. The final signal, which may be referred to as a final ECG signal, a cleaned ECG signal, a second ECG signal, or the like, may be displayed, recorded, and/or transmitted. Thus, any of the apparatuses described herein may include hardware, software and/or firmware for the display, recording and/or transmission of the final ECG signal. For example, any of these apparatuses may include a display, alarm, read-out, LED, or the like for presenting the processed signal and/or information extracted from the processed signal during or after processing. Any of these apparatuses may include a memory, storage, storage media, or the like for storing the processed signal and/or information extracted from the processed signal during or after processing. Any of these apparatuses may include a transmitter, receiver, transceiver, antenna, wireless connector, ultrasound transmitter, or the like, for transmitting the signal and/or information extracted from the processed signal during or after processing.

In general, the methods and apparatuses described herein are configured to operate on a starting signal by analyzing and signal to roughly identify putative regions of the ECG signal, and analyze the putative regions by correlating the regions with each other to determine identify highly correlated regions. Highly correlated regions may correspond to "typical" waveforms for in the initial signal. Such correlated regions may then be separately modified relative to the rest of the signal. For example, sub-regions (e.g., putative QRS regions) that are correlated with each other above a predetermined correlation threshold may be signal processed (e.g., filtered, amplified, and/or fit) using a first regime (e.g., filtering regime, etc.), the rest of the signal may be signal processed by a second regime (e.g., filtered, amplified, fit, etc.) and/or not processed. The processed signal then includes the putative sub-regions that have been processed by the first (e.g., filtering) regime within the rest of the signal that has been unprocessed or processed by a different, e.g., second, regime. The correlation results may be separately monitored, saved (e.g., as part of a matrix) and/or analyzed to determine or help determine indicator of cardiac health. The signal may be further processed, for example, by correlating (e.g., cross-correlating) other putative ECG regions and selectively/specifically processing correlated regions above a second predetermined correlation level as described above.

The cross-correlation of putative ECG regions in a signal (or a portion of a signal) may effectively determine which putative regions are "typical" of the signal. Thus, even in a noisy or low-sample-number signal, highly correlated regions may indicate that the overall or typical character of the signal, and the processing specific to the typical regions may preserve these similarities, particularly in ECG sub-regions that may be otherwise difficult to accurately filter or fit, such as R-wave, QRS regions, and the like. This technique, and the apparatuses and methods implementing it, may be adapted to collect relevant information during the processing steps, including information on the correlation, including the overall quality of the signal, regions of the signal that are highly correlated (or un-correlated), and the like.

For example, the techniques described herein and embodied in any of the apparatuses and methods described may include analyzing a signal to determine putative regions (e.g., identifying putative R-spikes and therefore putative QRS regions and/or R-R regions), cross-correlating these putative regions to correlated regions (one or more correlated "groups" of such sub-regions in the signal), and differentially processing the correlated putative regions (such as putative QRS regions); the process may be repeated for different sub-regions (such a putative R-R regions). Before, during or after these correlation steps, the entire signal may be processed using appropriate signal processing techniques such as filtering (bandpass, high-pass, low-pass, etc.).

Differential processing of sub-regions of the signal (e.g., correlated putative QRS regions) typically refers to processing of different regions of the signal by different techniques; other regions of the signal (including regions surrounding the processed sub-regions, may be processed by a separate technique or techniques. Differential processing may be performed by signal subtraction, for example, removing or copying the sub-regions to be processed (e.g., correlated QRS regions, correlated R-R regions, etc.) and processing them in isolation. The signal that they were copied or removed from may then be separately processed using a different processing technique (or left un-processed) and the processed sub-regions may be added back into the signal they were copied or removed from. In instances where the sub-regions were copied from the signal, they may be replaced with the processed sub-regions; in variations in which the sub-regions were removed, they may be added back in. The adjacent regions in the parent signal where the differentially processed sub-regions were copied/removed may be modified to smoothly connect to the sub-regions when they are put back into the parent signal. In some embodiments the correlated sub-regions may be processed while "in" the parent signal, without coping or removing them from the parent signal.

Any of the apparatuses or methods described herein may operate on digital signals. Thus, in any of these variations, the apparatus may be configured to receive or generate a digital data signal. For example, a system may include one or more electrode leads to record a signal from a patient's skin from which an ECG will be extracted. The system may include an analog-to-digital converter and pre-processing, including filtering, amplification and the like, to form a starting signal, which may be digital. Alternatively or in addition, any of these apparatuses may be configured to receive (e.g., read in) a digital data file including the starting signal. For example, a file may include single lead data (300 sample/sec 16 bit/binary, recorded from left hand/right hand). Any of the apparatuses (or methods) described herein may then pre-process the starting signal. For example, the starting signal may be processed to detect 50 or 60 Hz ("noise") mains, which may arise from power lines, etc., and then, if detected, remove them, for example, by bandpass filtering. This may be done via simple numerical integration. In some variations, notch filtering is done at 50 Hz, 60 Hz, or not at all. The bandpass filter may be hardware, software, firmware, or a combination; for example, this may be done with software filters, including standard, second-order, IIR filter.

Additional pre-processing of the starting signal (either before or after differential filtering) may include wavelet filtering. For example, the signal may be filtered by wavelet decomposition using soft thresholding on the wavelet coefficients down to level 5. Again, this filtering may be performed using software, hardware, firmware, or the like. For example, routines similar to Matlab's wavelet toolbox may be adapted for this, such as the function "cmddenoise". A wavelet can be chosen which looks like the main features in an ECG, minimizing distortion of the signal, particularly compared to a standard low pass or bandpass filter.

Pre-processing of the signal may also include removing baseline wander from the signal. Alternatively or additionally, baseline wander may be removed or reduced after an initial differential processing/correlation. For example, baseline wander may be corrected from the signal by determining a level in the signal and removing all long-wavelength components. Other techniques may be used, including cubic spline, etc. As mentioned, any of these techniques may be implemented by hardware, software, firmware of the like.

Although the apparatuses and method may be configured to operate on a signal with pre-processing, including some or all of the techniques mentioned above (removing line noise, wavelet filtering, removing baseline drift), in some variations, pre-processing is not used.

Thereafter, sub-regions of the ECG may be identified. For example, putative QRS regions may be detected or identified in the signal. Although the initial signal may be referred to a starting signal, as the signal is being processed as described herein, it may be referred to as an interim signal, putative ECG signal, modified signal, or "signal being processed".

One technique for identifying putative sub-regions that may be used by any of the apparatuses or methods described herein includes identifying R-spikes in the signal being processed. R-spikes are highly recognizable because they are typically rapid-onset/rapid-offset and large excursions. Thus numerous techniques may be implemented to identify them. Once identified, they may be themselves processed (e.g., correlated) or they may be used as landmarks to identify other putative ECG regions, such as QRS regions.

For example, any of the apparatuses and methods described herein may be configured to first identify putative QRS regions (e.g., using R-spikes). Correlations may then be applied by cross correlation of every putative QRS region against every other putative QRS region. The cross-correlation may be used to from a matrix or array. The array may include all of the cross-correlation information (including the correlation value, location, etc.) for the putative QRS regions, or it may include only a sub-set of them (e.g., those with correlation above a certain QRS threshold correlation value, or consecutive sequences of correlated QRSs, etc.

Unlike other techniques for analyzing and processing signals, the correlation techniques described herein, and embodied in the methods and apparatuses described work well on shorter signals, particularly compared to other techniques for analyzing signals of less than 30 seconds. The techniques described herein may be configured to operate on signals of between about 5 sec and about 10 sec, between about 5 sec and about 15 sec, between about 5 sec and about 20 sec, between about 5 sec and about 25 sec, between about 5 sec and about 30 sec, etc. The QRS determination performed by these apparatuses and methods may essentially determine "good" QRS wave regions even in a short, noisy signal. The QRS detection may essentially determine what beats in the signal may correspond to "real" beats. Thus, a correlation matrix may be used to provide additional insight for both cleaning the signal and for analyzing the signal. For example, the correlation matrix may be used to detect different types of beats, which may be identified by two or more correlated groups that don't cross-correlate. This technique is different, and in some ways superior to typical "binning" of beats or sub-regions of beats. For example, binning works only over long time stretches, with the longer times provided greater accuracy. In contrast the correlation techniques described herein may be used over even shorter times (e.g., less than two minutes, less than a minute, less than 50 sec, less than 40 sec, less than 30 sec, etc.). Typically, noise won't correlate.

As mentioned, in cross-correlating the putative sub-regions, every detected sub-region (e.g., putative QRS) is correlated with every other putative sub-region (e.g., putative QRS). For example, a QRS may be assumed to be 30 samples long, centered about the R-spike, and the putative QRS's are correlated by 'sliding' them over each other; the location of maximum correlations may be identified, which also be used to identify a possible offset, for example, if the max correlation doesn't occur with the R-spikes perfectly aligned. When the "correlation" between two signals is referred to, this correlation may be the maximum correlation when cross-correlating, or it may be a derivative of each correlation value as they are cross-correlated.

Identified sub-regions (e.g., putative QRS's) may be considered to be correlated if their correlation (e.g., peak correlation) is greater than a predetermined correlation threshold. For example, for putative QRS regions, a correlation threshold may be about 0.85 (e.g., 0.75, 0.80, 0.85, 0.90, etc.).

The longest sequence of consecutive, correlated QRS's may be found, and all other putative QRS regions which correlate with at least 3 other QRS regions from this long sequence ('good sequence') may be considered to also be 'good' QRS's. If the 'good sequence' is less than 6 beats long, the apparatus or method may indicate that the data may be too noisy, or too short. However, in general, the procedure may continue, for example, by finding the QRS regions which correlate with the most other QRS regions, and this QRS region may be taken to be 'good,' and all other QRS regions that correlate to it may be found. In some variations, the apparatus may be configured so that if there are less than 4 correlated QRS regions the processing stops. Based on the time/location of the peak correlation between the correlated QRS regions, the apparatus or method may be configured to correct the offset of any of the R-spikes.

Once the apparatus has determined the correlated sub-regions, these sub-regions may be differentially processed, compared to the rest of the signal, as mentioned.

Any of these apparatuses and methods may also determine an "average QRS" from the correlated QRS regions. For example, an average QRS may be constructed from all correlated QRS, each of which is 30 samples long. Typically, the average beat morphology won't change in a short time, even if the beat changes. Other techniques for determining an average QRS may be used. An average QRS may be used to calculate an onset/offset which may be used in subsequent processing and/or analysis.

For example, differential filtering on the signal being processed using the onset and offset of the average QRS to differentially modify the putative correlated QRS regions. For example, correlated QRS regions may be removed from the signal being processed (which may be referred to as signal "ybw" at this stage). The correlated QRS's may be filtered using Principal Component Analysis (PCA), and the rest of the signal (from which the QRS have been copied or removed) maybe is polynomial filtered. Thus the first filtering regime (processing regime) is PCA, and the second filtering regime is a polynomial filter. An example of a polynomial fit is Matlab's "sgolayfilt" function, which fits polynomials to a signal. The correlated QRS regions that have been processed may then be added back into the signal being processed (ybw). As mentioned, if the processed correlated QRS regions are added back into the signal, a local averaging may be done around the points where the QRS's were removed and added back in. The signal being processed may be referred to at this stage as post-first-correlation (yfinal in some of the figures below, although it may not be the final processed signal).

Although the apparatuses and methods may include a single correlation processing step (e.g., just QRS correlation as described above), in any of the variations described herein the apparatuses and/or methods may include correlation of a second putative ECG region, such as the R-R region. For example, an apparatus may be configured to build an RR-Beat Matrix that includes both putative and/or correlated QRS sub regions, as discussed above, and may also include putative and/or correlated R-R regions. As described above and illustrated in FIG. 9, the R-R region typically includes the interval between two QRS regions (every interval between adjacent R spikes). In some variations a separate matrix of R-R regions is generate and may be stored/analyzed. For example, an apparatus may build a matrix of all R-R intervals and scale them, and then correlates them. Building this matrix may allow the apparatus to identify noisy intervals, and label them as not correlated. Similarly, 'good' R-R regions may be identified. A discussed above, the sub-regions (R-R regions) may be cross-correlated and those sub-regions which are correlated above a pre-determined threshold may be identified as 'good'. In some apparatuses, regions having lower correlations may be referred to as putative "AFIB beats" and this lower correlation may be used in an AF detection (AfiB) mode for the apparatus or as part of an atrial fibrillation detection method.

For example, putative R-R sub-regions may be identified in the signal being processed (e.g., yfinal). Each putative R-R region (R-R beat) may be scaled to a given sample length, and an N×M matrix may be generated, where M is the number of putative R-R region and N is the sample length.

Every scaled R-R region may be correlated to every other scaled R-R region. A second matrix may be made that gives the square of the difference in duration of two given R-R regions. Putative R-R regions that correlate more than a pre-determined threshold (e.g., 0.76 or about 0.70, about 0.75, about 0.80, etc.) and in some variations that also vary by less than a predetermined threshold (e.g., 30%, or about 25%, about 30%, about 35%, etc.) in duration may be considered correlated. The R-R region that correlates with the most other beats may be identified, and considered as a "good" R-R region. All other R-R regions that correlate with this region may also be considered good. As mentioned R-R regions having a lower correlation to the 'good' regions may be identified for use for AF detection (which may be done in the same manner described, but using a lower correlation coefficient threshold (e.g., 0.65, 0.7, 0.75 that is lower than the correlation threshold for R-R regions), and no time duration constraint may be applied.

The apparatus may then differentially process the correlated putative R-R regions. For example, PCA may be performed on just the correlated putative R-R regions, and these correlated R-R regions may then be re-scaled to their original length. This additional correlation and differential processing may help clean up the final ECG signal that can be displayed, further analyzed or processed. In some apparatuses and/or methods this final correlation and differential processing is the final filtering step of the signal, and the final signal may be presented (e.g., displayed, stored, and/or transmitted). If one or more matrixes or extracted information was generated (e.g., an R-R matrix), this information may also be passed on. As mentioned, the creation of correlation matrixes may allow useful operation of these apparatuses and methods on even relatively short-duration signals, particularly as compared to other known techniques for signal processing of ECG signals.

The apparatuses and methods described herein may also be adapted to analyze ECG signals, either during the processing described above, or after, using the processed signal (e.g., yfinal, second ECG signal, etc.).

For example, the finally processed signal may be by an apparatus to generate an average beat. In some variations the apparatus may use only good (correlated) QRS regions and good (correlated) R-R regions to generate an average beat. For example, correlated QRS regions that are flanked on either side (overlap with) correlated R-R regions may be referred to as good P-QRS-T beats, and they may all be averaged together, and all of the good P-QRS-T beats are then correlated to this average. Any good P-QRS-T beats that correlate with lower than a threshold value (P-QRS-T correlation threshold) may be removed and the remainder (above threshold) can be averaged. A P-QRS-T threshold may be, for example, about 0.85 (e.g., about 0.8, about 0.85, about 0.90, etc.). The result may be referred to as a final average beat.

In addition, the apparatus may be configured to determine an interval calculation or any other derived indicator of cardiac fitness (e.g., cardiac wave morphology, R wave-ST segment, T wave amplitude analysis, etc.). For example the apparatus may be configured to calculate a P-R interval, QRS interval, etc. Such indicators may be determined from the average beat and/or from the cleaned final signal. For example, using the average beat, the QRS onset and offset, and T-wave offset may be found.

Finally, any variations of the apparatuses and methods described herein may be adapted to determine/detect atrial fibrillation. In general, an apparatus or method may be configured to operate on the starting signal and process it to include one or more correlations and differential processing techniques, as discussed above. Further, the apparatus or method may be adapted to analyze the ECG signal and/or components identified during the processing/correlating techniques to detect atrial fibrillation (AF). AF is known to have a characteristic erratic heart rate, with lot of change (variation) from beat to beat, which may be referred to as beat-to-beat variability. For example, in some variations the apparatus may be configured to examine the intervals of adjacent R-R intervals (either adjacent 'good'/correlated R-R intervals or both correlated and uncorrelated adjacent R-R intervals) and may determine a square of the difference.

Some apparatuses are configured to use various indicators to determine if an EMG indicates AF. For example, any of the apparatuses described herein may be configured to assess AF by looking at one or more of beat-to-beat variability, beat-to-every-other-beat variability, beat-to-every-third-beat variability, and the number of turning points of the RR-intervals. In addition, an apparatus may determine if a final, processed ECG waveform is indicative of atrial fibrillation by calculating a plurality of predictor beats from a window of n beats from the final, processed ECG signal as the window is moved though the final, processed ECG signal, where n is greater than some number of windows (e.g., 3, 4, 5, 6, 7, 8, 9, 10, etc.). An apparatus may also or additional look at the p-wave region of the average beat signal and/or the final processed signal.

Any of these apparatuses may also or alternatively detect AF by conditioning the analysis into three or more parts. For example, the apparatus may be configured to determine if an ECG signal is indicative of AF when the number of QRS regions (correlated QRS regions) is less than 35 by examining beat variability: a measure of beat-to-beat variability, a measure of beat-to-every-other-beat variability, and a measure of beat-to-every-third-beat variability; in addition, the apparatus may examine the number of turning points of the RR-intervals. The apparatus may indicate that a signal is likely to have AF with larger values of the first 3 (beat variability) indicators. The apparatus may also indicate that the ECG signal is likely to have AF if the signal does not have a small or large number of turning points. Thresholds for all 4 indicators may be chosen for a given run, and all 4 must be within/above threshold for an AF call. An apparatus may be configured to determine if an ECG signal indicates AF when there are more than 35 QRS regions in the signal by both looking at the number of turning points of the R-R intervals and also looking at error in the beat predictor formed by a running average (e.g., having a window size of n beats) as the window is run along the ECG signal. This may be implemented by applying a technique such as Sluter's algorithm. This algorithm may be based on using a 10 beat window before any given beat, and calculating the best predictor beat within that window for the given beat. This 10 beat window can be moved across the entire signal, and the best average predictor beat found. The error of this predictor beat is calculated, and if it is large-enough and the turning point value is within threshold, AF is called.

In some variations, the apparatus may determine AF by looking at the P waves of the ECG signal (e.g., the final signal and/or the average beat signal derived from the final ECG signal. P-waves may be identified using a template P-wave and correlating it with the average-beat signal before QRS onset. For example, the peak of the P-wave may be determined as a maximum value in the signal before the Q wave starts that is also a local maximum, and may be taken to the peak of the proposed p-wave to be used as the correlation point. The standard deviation of the proposed P-wave may also be calculated and compared to the standard deviation of the rest of the average beat signal before the Q-wave. The ratio of the standard deviation (std) of the proposed P-wave to the std of the remaining signal may be used as a weighting factor in determining the probability that the proposed P-wave is a P-wave. A final statistic may be calculated for P-wave probability for which 1 means perfect P-wave, while 0 and negative numbers indicate there is no P-wave. If the P-wave statistic is below a minimum threshold for the p-wave (e.g., about 0.25), AF is automatically called even if it was not called based on the other indicators. If the P-wave statistic is above a maximum threshold for the p-wave (e.g., of about 0.7) and the ratio of standard deviations is large-enough, a signal that was called AF based on the RR-statistics is corrected and called non-AF.

Any of the apparatuses described herein may be configured to analyze R-R statistics. These include basic statistics on all of the good R-R intervals (correlated). Any of the apparatuses described herein may be configured to examine a chain of indicators, as illustrated above. For example, an apparatus may examine a chain of indicators (HR variability, R-R crossings, etc.) ending with the P-wave detection test. This test/indicator may be used to correct the other tests. If the probably of the P wave detection is high enough, it may be used to remove a false positive result; for example, if the p-wave statistic is low enough, it may help determine a false negative.

For example, described herein are non-transitory computer-readable storage medium storing a set of instructions capable of being executed by a processor, that when executed by the processor, causes the processor to extract an electrocardiogram (ECG) signal from a signal by causing the processor to: identify putative QRS regions in a signal; cross-correlate the putative QRS regions to determine correlated QRS regions of the signal; and form a first ECG signal from the signal by filtering the correlated QRS regions of the signal using a first filtering regime and filtering a remainder of the signal outside of the correlated QRS regions using a second filtering regime that is different from the first filtering regime. Any of these non-transitory computer-readable storage medium (media) may also be configured to cause the processor to present the first ECG signal (e.g., display and/or transmit the first ECG signal. A non-transitory computer-readable storage medium may also be configured to further process the first ECG signal (which may also be referred to as a final ECG signal, a processed ECG signal, or the like).

For example, a non-transitory computer-readable storage medium may be further configured so that the set of instructions, when executed by the processor, further causes the processor to: identify putative R-R intervals in the first ECG signal; cross-correlate the putative R-R intervals to determine correlated R-R intervals in the first ECG signal; and modify the first ECG signal by filtering only the correlated R-R intervals of the first ECG signal with a third filtering regime.

The set of instructions, when executed by the processor, may further cause the processor to pre-filter the signal before identifying putative QRS regions in the signal. For example, the set of instructions, when executed by the processor, may further cause the processor to remove 50 Hz or 60 Hz noise in the signal before identifying putative QRS regions in the signal. The set of instructions, when executed by the processor, may further cause the processor to perform wavelet filtering on the signal before identifying putative QRS regions in the signal. The set of instructions may further cause the processor to identify putative QRS regions in a signal by filtering the signal, setting a threshold, and identifying spikes above the threshold as putative R-spike components of putative QRS regions.

The set of instructions may further cause the processor to calculate a putative heart rate (HR) from the R-spikes and to use the HR to modify the signal to remove baseline wander.

The set of instructions may further cause the processor to cross-correlate the putative QRS regions to determine correlated QRS regions of the signal by cross-correlating each putative QRS region with every other putative QRS region. The set of instructions may further cause the processor to determine correlated QRS regions of the signal when a peak correlation between a pair of putative QRS regions is above a correlation threshold and their amplitudes vary by less than an amplitude threshold. For example, the correlation threshold may be substantially 0.8 and the amplitude threshold may be substantially 40%.

The set of instructions may further cause the processor to indicate that there may be a problem with the signal when there are fewer than a minimum number of correlated consecutive putative QRS regions.

For example, the minimum number of correlated consecutive putative QRS regions may be 6.

The set of instructions may further cause the processor to form a first ECG signal from the signal by removing the correlated QRS regions from the signal to form a subtracted signal, filtering the correlated QRS regions of the signal using the first filtering regime and filtering the subtracted signal comprising the remainder of the signal outside of the correlated QRS regions using the second filtering regime, and then adding together the filtered correlated QRS regions with the filtered subtracted signal.

The set of instructions may further cause the processor to form a first ECG signal from the signal by filtering the correlated QRS regions of the signal using a first filtering regime comprising a Principle Component Analysis (PCA).

The set of instructions may further cause the processor to form a first ECG signal from the signal by filtering the remainder of the signal outside of the correlated QRS regions using a second filtering regime comprising a polynomial fit to the remainder of the signal outside of the correlated QRS regions.

The set of instructions may cause the processor to identify putative R-R intervals in the first ECG signal by constructing an R-R matrix of normalized R-R intervals from the first ECG signal.

The set of instructions may further cause the processor to cross-correlate the putative R-R intervals to determine correlated R-R intervals in the first ECG signal by cross-correlating every normalized R-R interval in the R-R matrix against every other normalized R-R interval in the matrix.

The set of instructions may further cause the processor to determine correlated R-R intervals when a correlation coefficient threshold between R-R intervals is above an R-R correlation threshold. For example, the R-R correlation threshold may be substantially 0.7.

The set of instructions may further cause the processor to modify the first ECG signal by filtering only the correlated R-R intervals of the first ECG signal with a Principle Component Analysis (PCA) of the correlated R-R intervals.

Any of the apparatuses or methods (e.g., the set of instructions) described herein, may further determine if the signal is indicative of an atrial fibrillation.

For example, a set of instructions may further cause the processor, further causes the processor to indicate if the signal is indicative of an atrial fibrillation by comparing the beat-to-beat variability of the first ECG signal.

The set of instructions may further cause the processor, further causes the processor to calculate an average beat by averaging correlated QRS regions that overlap on either side by correlated R-R intervals to form an intermediate average, and then correlating the intermediate average with correlated QRS regions that overlap on either side by correlated R-R intervals, and averaging those correlated QRS regions that overlap on either side by correlated R-R intervals that correlate with the intermediate average by greater than a threshold of substantially 0.85, to form the average beat.

The set of instructions may further cause the processor to determine a QRS onset, QRS offset, and T-wave offset from the average beat.

Also described herein are non-transitory computer-readable storage medium storing a set of instructions capable of being executed by a processor, that when executed by the processor, causes the processor to extract an electrocardiogram (ECG) signal from a signal by causing the processor to: identify putative QRS regions in a signal; cross-correlate the putative QRS regions to determine correlated QRS regions of the signal; and form a first ECG signal from the signal by differentially filtering the correlated QRS regions of the signal relative to a remainder of the signal outside of the correlated QRS regions; identify putative R-R intervals in the first ECG signal; and cross-correlate the putative R-R intervals present the first ECG signal to determine correlated R-R intervals in the first ECG signal; and modify the first ECG signal by differentially filtering the correlated R-R intervals of the first ECG signal relative to a remainder of the signal outside of the correlated R-R intervals.

Also described herein are non-transitory computer-readable storage medium storing a set of instructions capable of being executed by a processor, that when executed by the processor, causes the processor to extract an electrocardiogram (ECG) signal from a signal by causing the processor to: identify a plurality of putative QRS regions in a signal; cross-correlate each of the putative QRS regions with each other to identify correlated QRS regions; forming a first ECG signal by: filtering a portion of the signal corresponding to the correlated QRS regions using a first filtering regime; and filter a second portion of the signal corresponding to a region of the signal excluding the correlated QRS regions with a second filtering regime that is different from the first filtering regime; identify putative R-R intervals in the first ECG signal; cross-correlate the putative R-R intervals to determine correlated R-R intervals; modify the first ECG signal by filtering only the portion of the first ECG signal corresponding to the correlated R-R intervals with a third filtering regime; and display the first ECG signal.

Also described herein are systems for extracting ECG information from a signal. For example, a system may include: a QRS identifying module configured to receive an electrical signal and to identify a plurality of putative QRS regions in the signal; a QRS cross-correlator coupled to the QRS identifying module configured to cross-correlate each of the putative QRS regions with each other; a QRS filter module coupled to the QRS cross-correlator and configured to modify the signal by differentially filtering correlated QRS regions of signal relative to other regions of the signal; an R-R cross-correlator adapted to receive the modified signal from the QRS filter module and to cross-correlate putative R-R intervals in the modified signal with each other; and an R-R filter module coupled to the R-R cross-correlator and configured to further modify the modified signal by differentially filtering correlated R-R intervals relative to other regions of the modified signal.

A system may also include a pre-filtering module connected to the QRS identifying module and configured to pre-filter the received signal before it is passed to the QRS identifying module. A system may also include an atrial fibrillation detection module configured to receive the further modified signal from the R-R filter module and to output an indicator if the further modified signal is indicative of atrial fibrillation. The QRS identifying module may comprise an R-wave detection module having a band pass filter and moving window integrator.

Any of the apparatuses and methods described herein may be configured to determine one or more indicator of cardiac health. For example, any of the apparatuses and methods described herein may be configured to determine one or more indicators of atrial fibrillation from a starting signal. Thus, described herein are non-transitory computer-readable storage medium storing a set of instructions capable of being executed by a processor, that when executed by the processor, causes the processor to determine if an electrocardiogram (ECG) signal is indicative of atrial fibrillation, by causing the processor to: identify putative QRS regions in a signal; cross-correlate the putative QRS regions to determine correlated QRS regions of the signal; and form a first ECG signal from the signal by differentially filtering the correlated QRS regions of the signal relative to a remainder of the signal outside of the correlated QRS regions; identify putative R-R intervals in the first ECG signal; and cross-correlate the putative R-R intervals present the first ECG signal to determine correlated R-R intervals in the first ECG signal; modify the first ECG signal by differentially filtering the correlated R-R intervals of the first ECG signal relative to a remainder of the signal outside of the correlated R-R intervals; and determine if the first ECG signal is indicative of atrial fibrillation. For example, the set of instructions may cause the processor to determine if the first ECG signal is indicative of atrial fibrillation by examining the number of turning points of R-R intervals in the first ECG signal.

The set of instructions may cause the processor to determine if the first ECG signal is indicative of atrial fibrillation by examining the number of turning points of correlated R-R intervals in the first ECG signal.

The set of instructions may cause the processor to determine if the first ECG signal is indicative of atrial fibrillation by measuring beat-to-beat variability, beat-to-every-other-beat variability, and beat-to-every-third-beat variability. The set of instructions may cause the processor to determine if the first ECG signal is indicative of atrial fibrillation by measuring beat-to-beat variability, beat-to-every-other-beat variability, and beat-to-every-third-beat variability and by examining the number of turning points of R-R intervals in the first ECG signal. The set of instructions may cause the processor to determine if the first ECG signal is indicative of atrial fibrillation by calculating a plurality of predictor beat from a window of n beats in the first ECG signal as the window is moved though the first ECG signal, where n is greater than three. The set of instructions may cause the processor to determine if the first ECG signal is indicative of atrial fibrillation by calculating a plurality of predictor beat from a window of n beats in the first ECG signal as the window is moved though the first ECG signal, where n is substantially 10 or more.

The set of instructions may cause the processor to determine if the first ECG signal is indicative of atrial fibrillation by calculating a plurality of predictor beat from a window of a n beats in the first ECG signal as the window is moved though the first ECG signal, where n is greater than three and by examining the number of turning points of R-R intervals in the first ECG signal. The set of instructions may cause the processor to determine if the first ECG signal is indicative of atrial fibrillation by calculating an average beat from the first ECG signal and correlating a proposed P-wave with the region of the average beat before the QRS onset of the average beat.

The set of instructions may cause the processor to calculate an average beat by averaging correlated QRS regions that overlap on either side by correlated R-R intervals to form an intermediate average, and then correlating the intermediate average with correlated QRS regions that overlap on either side by correlated R-R intervals, and averaging those correlated QRS regions that overlap on either side by correlated R-R intervals that correlate with the intermediate average by greater than a threshold of substantially 0.85, to form the average beat.

Methods of extracting ECG information from a starting signal, including methods for extracting an ECG signal, and/or methods of identifying an indicator of cardiac health (such as a method of identifying atrial fibrillation) from and ECG are also described. For example, described herein are computer implemented methods for extracting an electrocardiogram (ECG) signal from a signal comprising the steps of: identifying putative ECG sub-regions in a signal; cross-correlating the putative sub-regions to determine correlated sub-regions of the signal; and forming a first ECG signal from the signal by filtering the correlated sub-regions of the signal using a first filtering regime and optionally filtering a remainder of the signal outside of the correlated sub-regions using a second filtering regime that is different from the first filtering regime.

Also described are computer implemented methods for extracting an electrocardiogram (ECG) signal from a signal comprising the steps of: identifying putative QRS regions in a signal; cross-correlating the putative QRS regions to determine correlated QRS regions of the signal; and forming a first ECG signal from the signal by filtering the correlated QRS regions of the signal using a first filtering regime and optionally filtering a remainder of the signal outside of the correlated QRS regions using a second filtering regime that is different from the first filtering regime.

Also described are computer implemented methods for extracting an electrocardiogram (ECG) signal from a signal comprising the steps of: identifying putative R-R intervals in the signal; cross-correlating the putative R-R intervals present the signal to determine correlated R-R intervals in the signal; forming a first ECG signal by differentially filtering the correlated R-R intervals of the first ECG signal relative to a remainder of the signal outside of the correlated R-R intervals.

Any of these computer implemented methods may also include the steps of, prior to the step of identifying putative R-R intervals, identifying putative QRS regions in the signal, cross correlating the putative QRS regions to determine correlated QRS regions, forming a further signal by filtering the correlated QRS regions and performing the remaining steps of the method using the further signal.

Any of these computer implemented methods may be part of an apparatus, such as a device, that is configured to perform the method.

For example, described herein are electronic devices for identifying atrial fibrillation configured to identify putative R-R intervals in the signal; cross-correlate the putative R-R intervals present the signal to determine correlated R-R intervals in the signal; form a first ECG signal by differentially filtering the correlated R-R intervals of the first ECG signal relative to a remainder of the signal outside of the correlated R-R intervals, and provide an indication if the first ECG signal is indicative of atrial fibrillation.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 8 illustrates multiple steps of different sections, any of the apparatus and methods described herein may include only a portion of processing techniques shown in FIG. 8; for example, a method or apparatus for extracting an ECG may only incorporate the techniques illustrated on the left-hand side of the figure (generating signal "yf" and/or generating signal "yfinal").

DETAILED DESCRIPTION

Described herein are apparatuses and methods for extracting (e.g., de-noising, cleaning, filtering, etc.) an ECG signal from a starting signal, as well as apparatuses and methods for determining one or more indicator of cardiac health/function (including, but not limited to atrial fibrillation). In general, the apparatuses described herein (including systems and devices) may perform all or some of the procedures described herein. A device may receive a starting signal (e.g., an ECG recording) either directly (from connected electrodes) or indirectly, by receiving an ECG signal and/or digital file including ECG information. ECG information maybe single lead or multiple lead. For example, ECG information may be single-channel ECG information. The system or device may then operate on this information and provide novel and specific output based thereon. For example, a system may display one or more signals indicative of one or more cardiac properties, functions or dysfunctions, including atrial fibrillation. In some variations the system may analyze the ECG information and modify it for later review, including appending comments and/or analysis regarding the ECG information. In some variations, the system organized the ECG signals (or sub-regions of the ECG signals) in some manner, e.g., collecting similar (correlated) signals or sub-regions of signals. The system may be configured to alert the user, medical professional, or other (including other systems) of the results of the operations on the ECG information.

Figure 2:
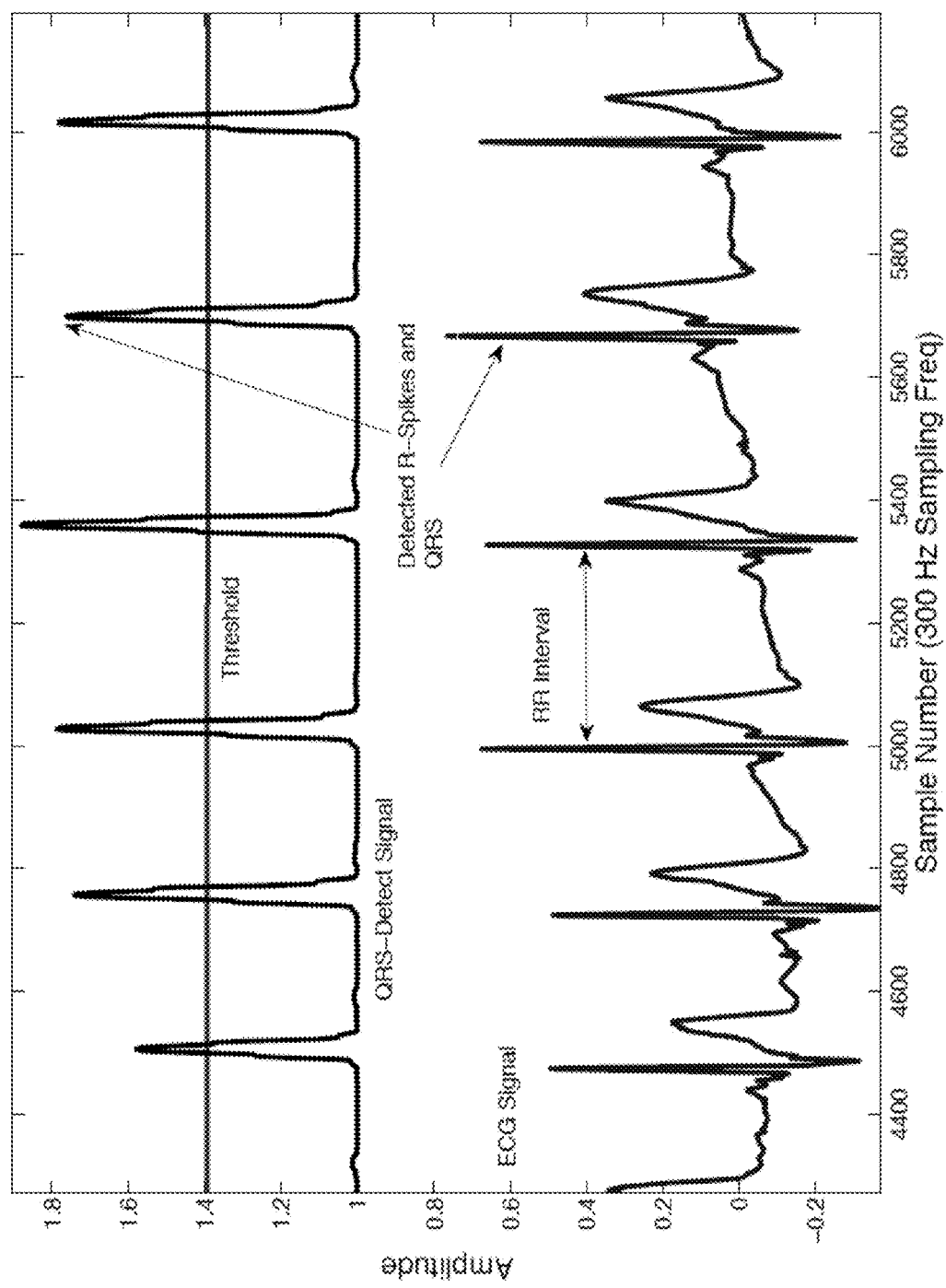
FIG. 2. Shows an example of an ECG signal on the bottom, and the corresponding signal used to detect the QRS complexes. The upper curve is the signal after the wavelet filtering procedure is performed. The horizontal line is the dynamic threshold. Any excursion of the signal above the threshold indicates an R-wave of a QRS complex.
Figure 9:
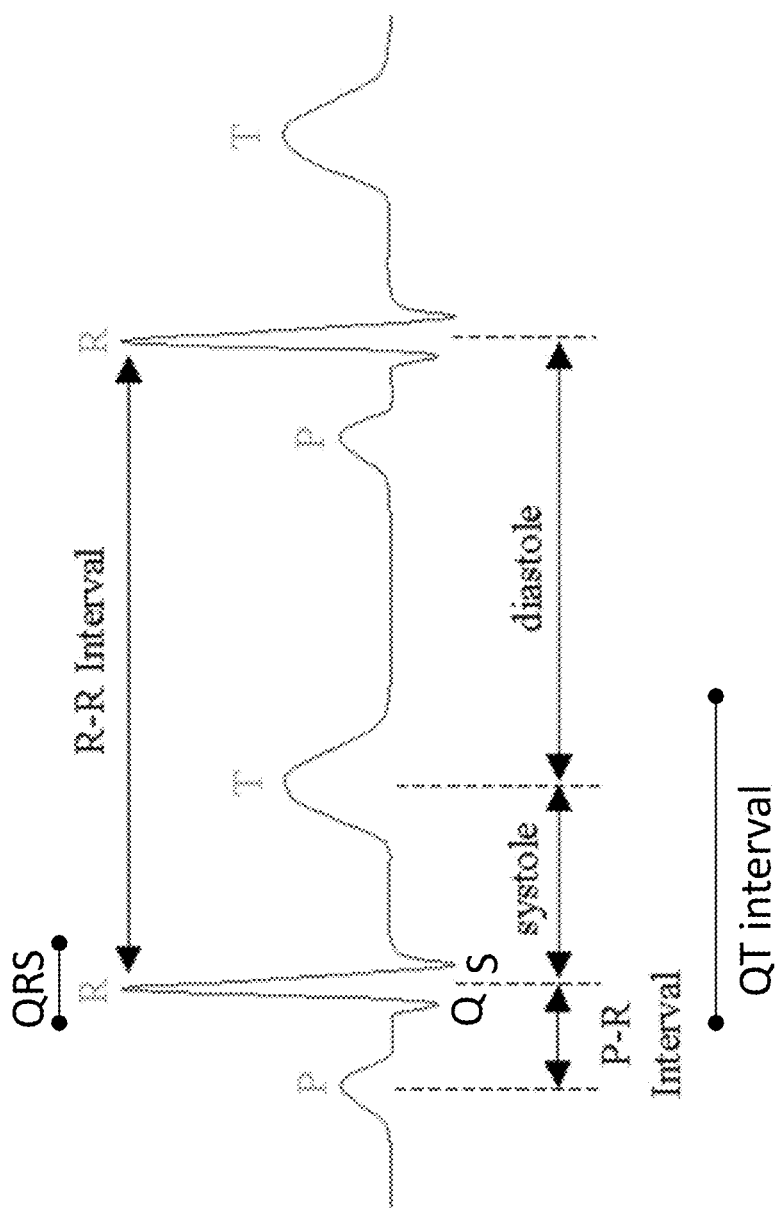
FIG. 9 is an idealized version of an ECG trace, showing two cycles, including characteristic regions such as the QRS complex, the R-spike, and the R-R interval.

In general, the apparatuses and methods described herein operate on a starting signal such as a signal read from a single lead of a pair of ECG electrodes, and extracts a cleaned-up version of an ECG trace, which may include multiple ECG "beats" by identifying putative sub-regions of in the signal, cross-correlating these sub-regions against each other, and using the correlation information to determine correlated sub-regions that are then differentially processed relative to the rest of the signal. Thus the correlated putative sub-regions are processed (filtered, amplified, fit, etc.) differently than the non-correlated putative sub-regions and the rest of the waveform except for the putative correlated sub-regions. The resulting signal includes both the correlated sub-regions and the rest of the signal. In general, a sub-region of an ECG signal may include any characteristic region of an ECG beat or beats, such as those illustrated in FIGS. 2 and 9, for example, P-waves, R-waves, Q-waves, S-waves, T-waves, QRS regions, P-R intervals, R-R intervals, etc.

Any of the processes described herein may be performed on a dedicated device that is configured specifically to perform some or all of these functions. Also included herein are software, hardware and/or firmware configured to perform these functions. Any of the data or information derived may be stored and/or operated on using non-volatile memory, hardcopy, printouts, or other storage, analysis and communication techniques.

Figure 8:
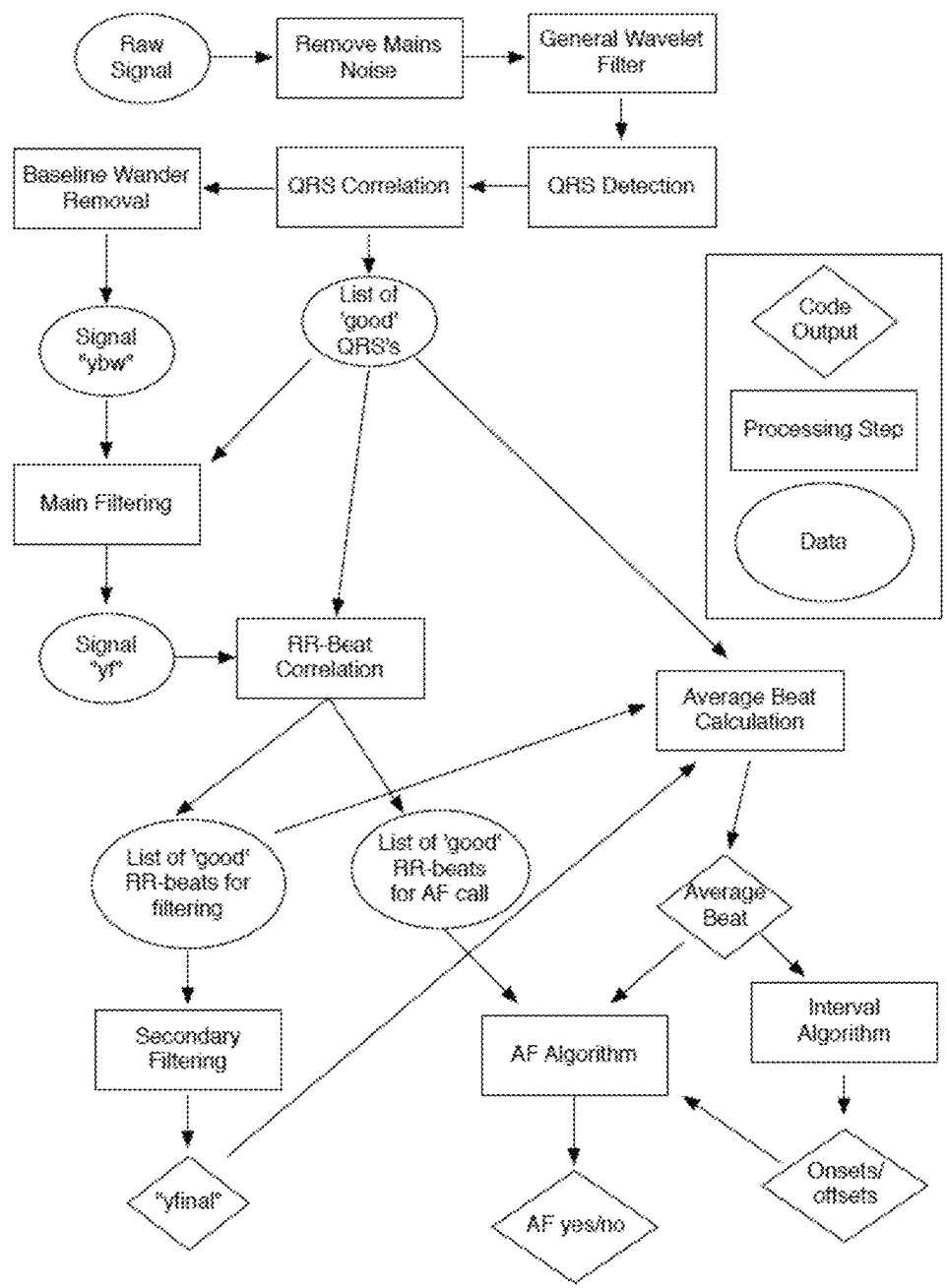
FIG. 8 is an exemplary flowchart for the process of analyzing the ECG (single-lead) data as described herein, including the automatic detection of cardiac events such as atrial fibrillation. Although

For example, FIG. 8 illustrates a flowchart of exemplary techniques; some of the techniques included in FIG. 8 are optional. These techniques, which may be incorporated into an apparatus and/or method, are described below and illustrated in the figures. For example, described below are apparatuses incorporating some of these processes. A system or device as described herein may be configured to all or some of these procedures.

For example, described below are techniques that may be performed by any of the apparatuses described herein and may part of any method. Examples of these techniques include pre-filtering (such as detection of mains, filtering of mains, wavelet filtering, etc.), sub-region detection (e.g., QRS detection, R-R detection), baseline wander removal, cross-correlation (QRS correlation, R-R correlation), differential processing (QRS filtering, R-R filtering, subtracted signal filtering, etc.), average beat calculation, interval calculation, and cardiac health analysis (e.g., atrial fibrillation detection, etc.). Performance of any of these techniques may be implemented in any of the apparatuses described, and/or any of the methods described. Some of these techniques may be omitted. Sections 1-12 below illustrate one example of some of these techniques, and are not intended to be limiting. The order of performance, and/or the inclusion, of any of these techniques may be varied. In addition, where specific ECG sub-regions are indicated (e.g., QRS, R-R, etc.) the technique may be adapted to any other sub-region.

1. Pre-Filtering

Analysis and pre-filtering may be included. For example, 50 Hz or 60 Hz signals may be analyzed. In some variations, data (a starting signal or starting ECG signal) is received by the apparatus for processing. Fourier coefficients at 9 different frequencies are calculated ranging from 10 to 100 Hz. If the 50 Hz component is larger than the others then mains noise is set at 50 Hz. The same check is done for 60 Hz. If neither 50 Hz nor 60 Hz components are larger than the other components, then no mains filtering is performed. Notch filter is implemented at 50 Hz, 60 Hz, or not at all. This may be done, for example, using MatLab's filter function, implementing a standard, second-order, IIR filter.

2. Pre-Filtering 2: Wavelet Filtering

Figure 1:
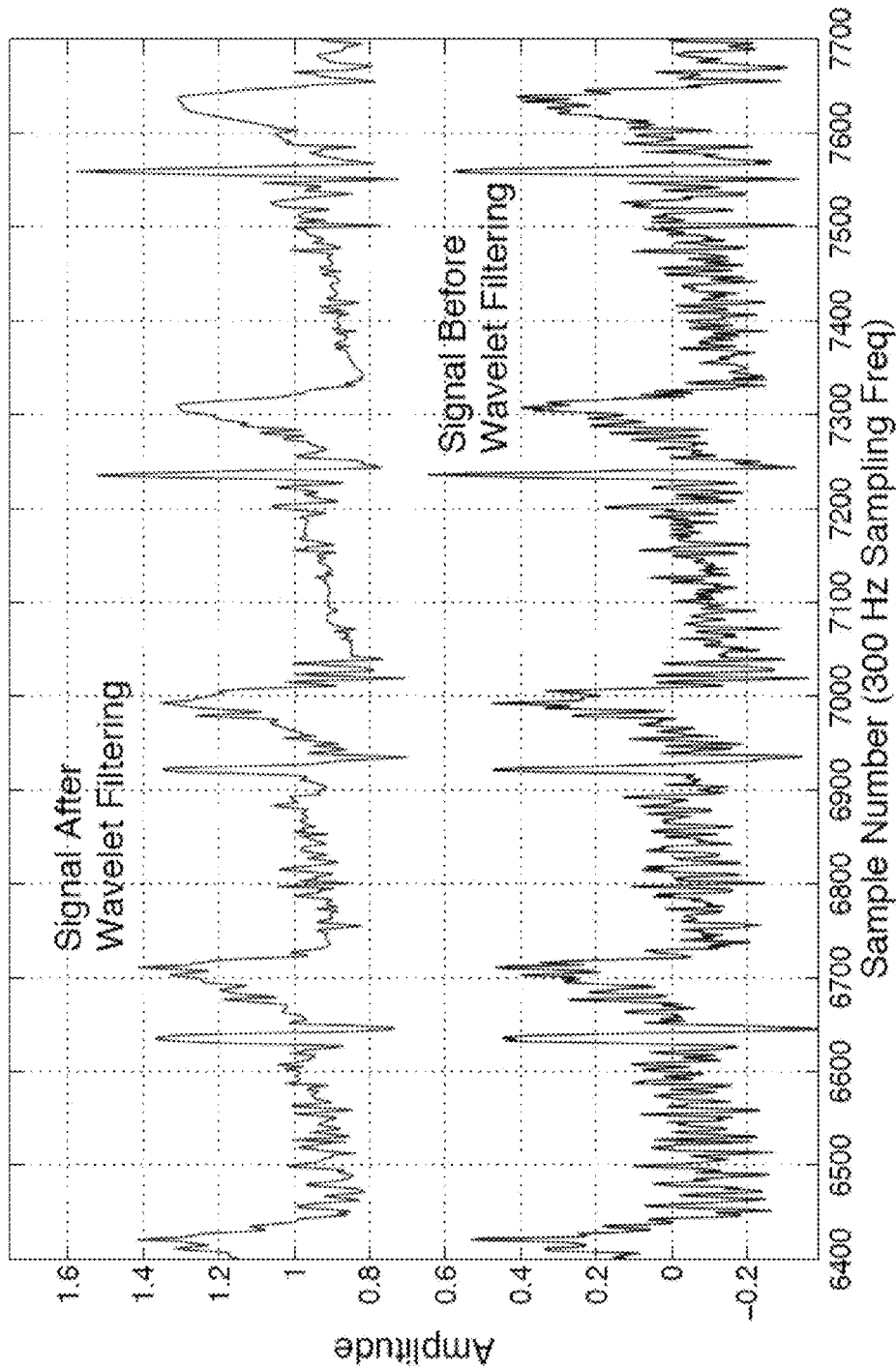
FIG. 1 is an example showing the wavelet filtering using the function cmddenoise. The lower curve is the raw ECG data (there was no mains noise detected). The upper curve is the raw data after wavelet filtering.

The starting signal may be filtered by wavelet decomposition using soft thresholding on the wavelet coefficients down to level 5. Matlab's wavelet toolbox may be used for this, specifically the function cmddenoise. Because a wavelet can be chosen which resembles the main features in an ECG, this process does not distort the signal as much as a standard low-pass or bandpass filter. This technique does not required MatLab, as it may be implement using other similar functions or may be implemented "by hand". Wavelet filtering of the entire signal may improve subsequent QRS detection. FIG. 1 illustrates an example of wavelet filtering on a starting signal.

3. Sub-Region Detection: QRS Detection

In general, any of the apparatuses may be configured to determine the time/locations of various sub-regions of the ECG in the signal. This may be done by identifying putative R-regions, for example. In one example, the method of detecting R-waves is derived from a method based: Band Pass IIR filter->derivative->square->moving window integrator. In this example, the MatLab function filter is used, implementing a series of standard FIR filters.

The resulting signal may be dynamically thresholded. Spikes extending above the threshold indicate R-spikes (see FIG. 2). The exact R-spike locations are detected by looking for the maximum square of the bandpass-filtered signal between the location where the moving-window-integrated signal goes above the threshold and the location where the signal then goes below the threshold.

Based on all of the detected R-spikes, an average RR interval may be found and a preliminary heart rate (HR) calculated.

4. Baseline Wander Removal

Using the HR from step (3), a certain wavelet level is calculated and used to remove baseline wander. Wavelet coefficients at the calculated level are set to zero and the signal is reconstructed. The resulting ECG signal with baseline wander removed is called "ybw". The MatLab internal functions wavedec and waverec are used. These functions deconstruct/reconstruct a signal using dyadic scales.

5. Correlations

Figure 3:
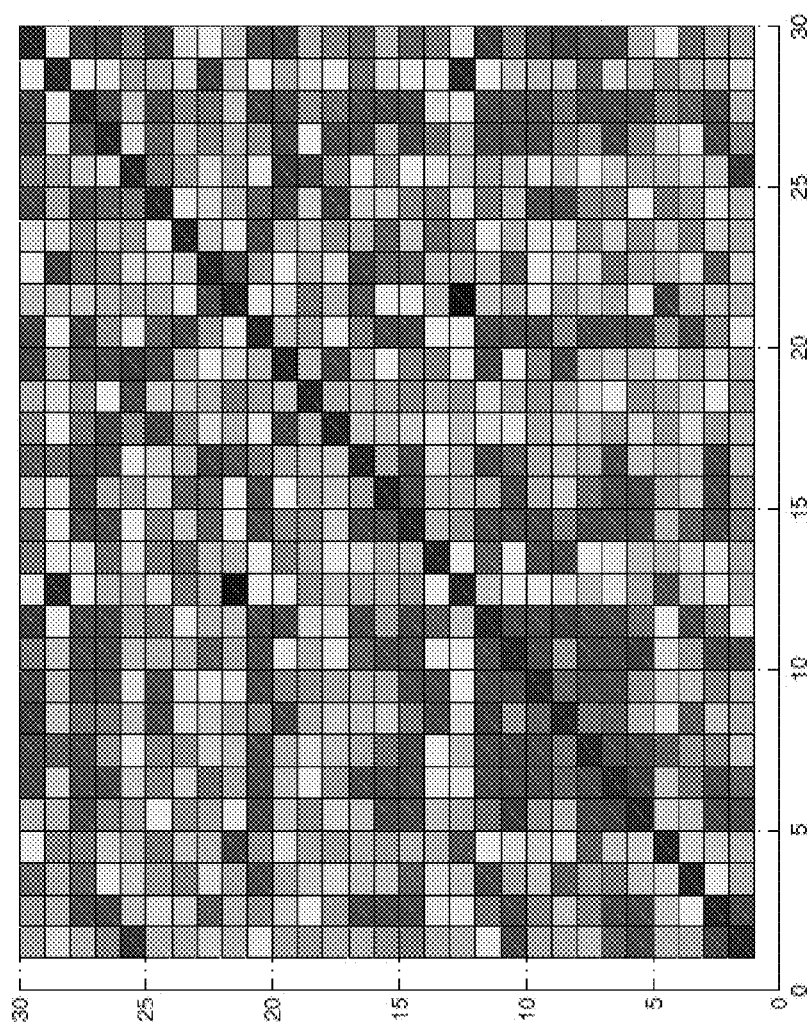
FIG. 3 Shown is the QRS correlation matrix for the ECG signal in FIG. 1. Darker shades indicate high positive or high negative correlation. As each QRS correlates with itself perfectly, the diagonal is dark. One can see a grouping of correlated QRS's in the middle of the lower left quadrant.

In this example, the apparatus cross-correlates every putative sub-region (e.g., QRS) with every other putative QRS to identify the highly (above a predetermine QRS correlation threshold (e.g., 0.85). For the correlation, the QRS's are assumed to be 30 samples long, centered on the R-spikes. For every two QRS's, a sliding correlation is calculated by off-setting the QRS's from one to 32 samples. The location of maximum correlations is found as well as possible offsets (if max correlation doesn't occur with the R-spikes perfectly aligned). Shown in FIG. 3 is the correlation matrix for the ECG signal shown in FIG. 1. Dark blocks indicate high positive correlation and lighter colors indicates high negative correlation.

In this example, QRS's are considered to be correlated if their peak correlation is greater than 0.8 and their amplitudes vary by less than 40%. The longest sequence of consecutive, correlated QRS's is found, and the QRS's which comprise this sequence are considered 'good' QRS's. All other QRS's that correlate with at least 3 of these 'good' QRS's are also considered good.

If the initial 'good sequence' is less than 6 beats long, the apparatus may tell you that the data may be too noisy, or too short. The apparatus may still proceed though, and finds the QRS which correlates with the most other QRS's. This QRS is taken to be 'good', and all other QRS's which correlate to it are found and called 'good'.

During this technique, all of the R-spikes are corrected for possible offsets.

Correlating all of the detected QRS's in this way allows for the rejection of QRS's which are contaminated with noise.

It may be desired that contaminated QRS's not be used in any average beat. Furthermore, any other noise which was detected initially as a QRS will be rejected. This allows the initial QRS detection to be over sensitive.

6. Average Sub-Region (e.g., QRS)

An average QRS is found from all the correlated 'good' QRS's, each of which are 30 samples long. The onset and offset of the average QRS are found.

7. Primary (Differential) Filtering or Correlated Sub-Regions

Using the onset and offset of the average QRS, all of the correlated QRS's can be removed from the signal "ybw". The QRS's may be filtered using Principal Component Analysis (PCA), and the remaining QRS-removed signal is polynomial filtered with Matlab's sgolayfilt function, which consists of fitting polynomials to a signal. The QRS's are then added back in.

Figure 4:
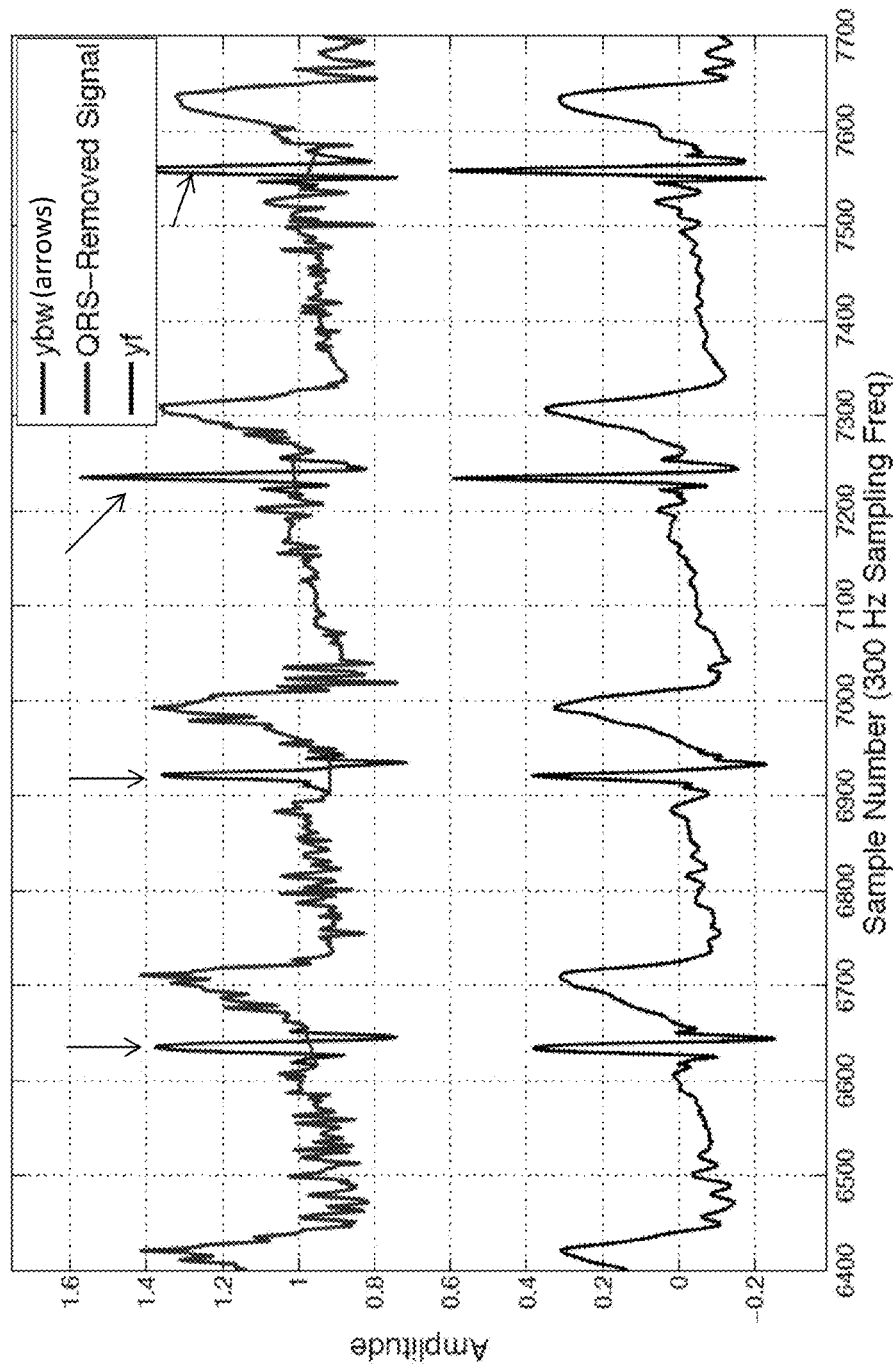
FIG. 4 shows an example of main filtering on a noisy ECG. The arrows pointing to the somewhat smoother upper dark curve regions are "ybw" (the correlated QRS regions after differential filtering), which are calculated by removing baseline wander from starting trace (upper curve) in FIG. 1. The regions of the upper curve that are 'noisy' are the QRS-removed signal. The bottom curve is a signal "yf", which is generated by differentially processing the upper curve (separately processing the correlated QRS regions), performing PCA on the correlated QRS complexes and Golay filtering on the QRS-removed signal.

A local averaging is implemented around the points where the QRS's were removed and added back in, resulting in signal "yf". FIG. 4 shows the steps of this filtering process.

8. Building a Matrix (R-R Beat Matrix)

R-R beats are defined as intervals between two adjacent R-spikes. The signal "yf" is broken up into R-R beats. Every R-R beat is scaled to a given sample length, and an N×M matrix may be constructed, where M is the number of RR-beats and N is the given sample length.

Figure 5:
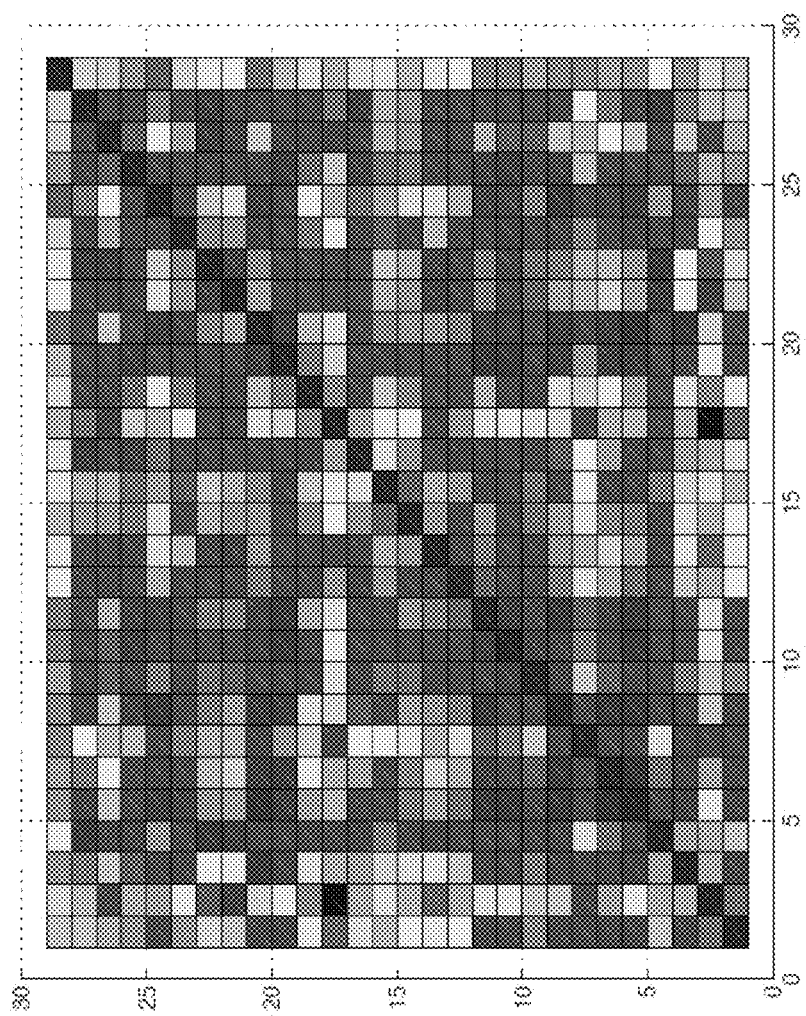
FIG. 5 shows an RR-beat correlation matrix using the ECG signal from FIGS. 1, 3, and 4. Darker squares indicate high positive or high negative correlation. As each beat correlates with itself perfectly, the diagonal is dark. One can see that RR-beat number 2 does not correlate well with any of the other RR-beats.

Every scaled RR-beat is correlated to every other scaled RR-beat. A second matrix is also constructed which gives the square of the difference in duration of two given RR-beats. Any two given RR-beats that have a correlation coefficient of more than 0.75 and vary by less than 30% in duration are considered correlated. The RR-beat which correlates with the most other RR-beats is found, and considered 'good'. All other RR-beats which correlate with this beat are also considered 'good'. Shown in FIG. 5 is the RR-beat correlation matrix.

This process if repeated using a correlation coefficient threshold of 0.7 and no time duration constraint, resulting in another set of RR-beats which are used for AF detection, see section 12. There are two main purposes of correlating RR-beats. First, noise may be introduced in the ECG signal between two QRS complexes and this noise may distort a final average beat. RR-beat correlation corrects for this. Second, PCA analysis is performed on all of the 'good' RR-beats, and this further cleans up the ECG signal.

9. Secondary Filtering: PCA on Good RR-Beats

Figure 6:
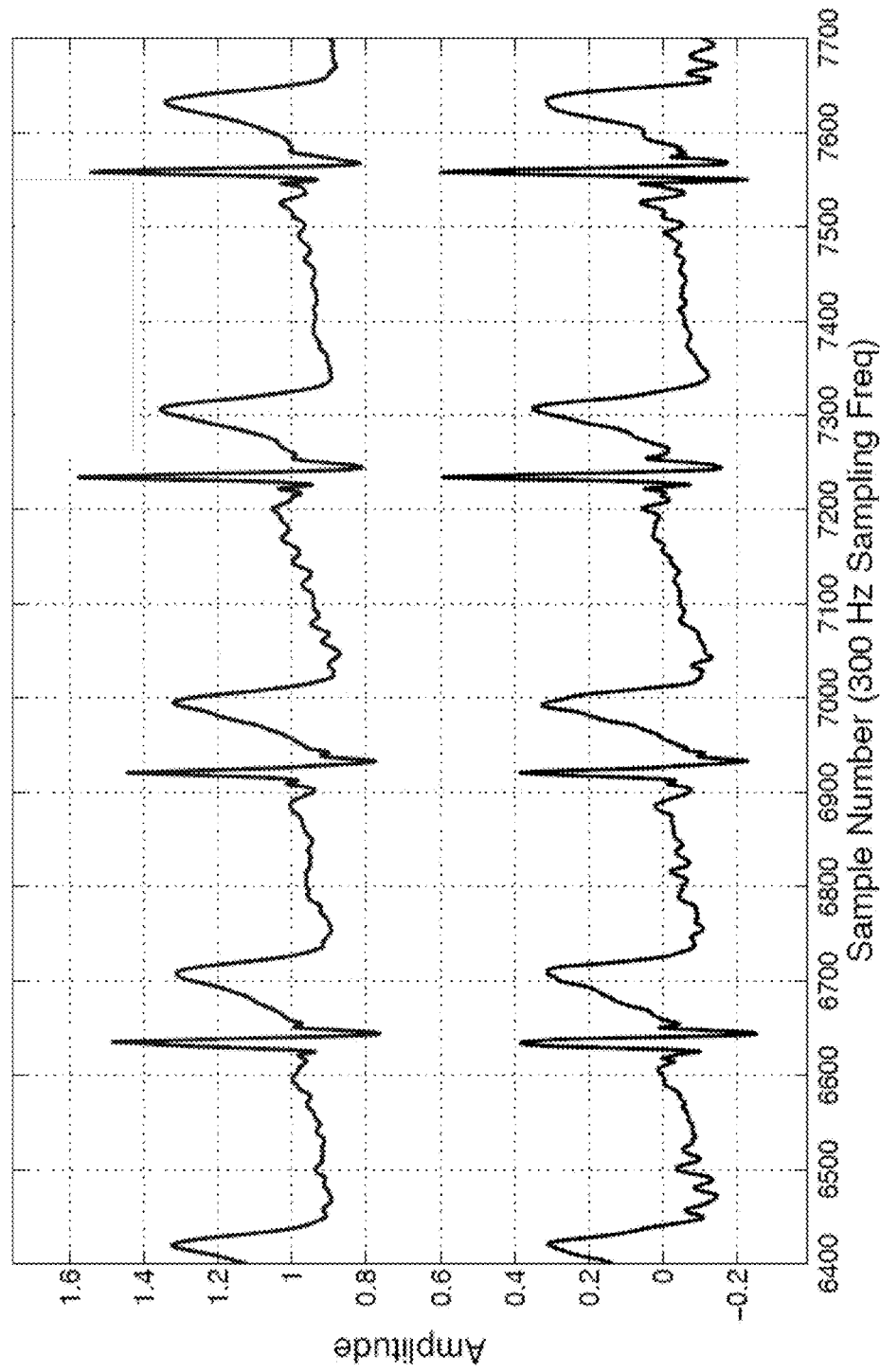
FIG. 6 is an example showing the effect of secondary filtering. The bottom curve is the signal "yf" from FIG. 4. The upper curve is the signal "yfinal" resulting from differential filtering on correlated R-R sub regions.

PCA is implemented on all of the 'good' RR-beats, and then the RR-beats are re-scaled to their original length. This does not have a direct effect on the final average beat displayed in the pdf reports, interval measurements, or HR calculation or AF determination. However this further cleans up an ECG signal. This process operates on the signal "yf", producing signal "yfinal", which is the signal displayed in the pdf reports. FIG. 6 shows the effects of secondary filtering on an ECG signal.

10. Average Beat Calculation

Good P-QRS-T beats are taken to be beats in which a good QRS is surrounded on either side by good RR-beats. All of these 'good' P-QRS-T beats are averaged.

Figure 7:
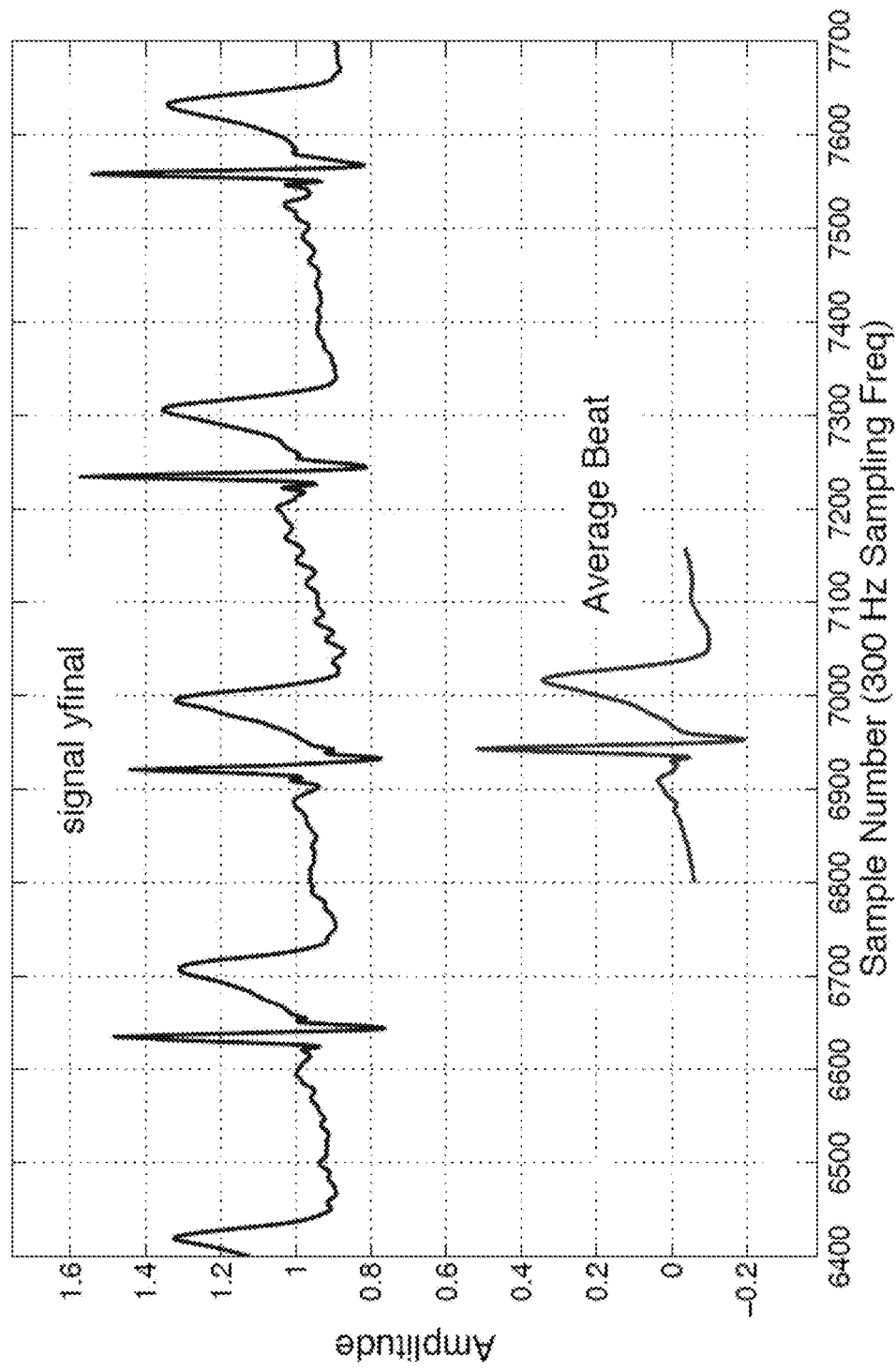
FIG. 7 shows in the upper curve, a signal "yfinal" from FIG. 6 as well as an averaged beat (below it) that is calculated from all of the "good" P-QRS-T intervals as described herein.

All of the good P-QRS-T beats are then correlated to the average. Ones with lower than 0.85 correlations are rejected, and the average is re-calculated. This gives the final average beat displayed in the pdf reports and shown in FIG. 7.

11. Interval Calculation

Using the average beat, the QRS onset and offset, and T-wave offset are found. These intervals are marked in the pdf reports.

12. AF Detection

AF detection may be broken up into 3 parts. First, if the number of QRS complexes is less than 35, four AF indicators are calculated based on beat variability. The first indicator is a measure of beat-to-beat variability. The second is a measure of beat-to-every-other-beat variability, and the third is a measure of beat-to-every-third-beat variability. The fourth indicator is the number of turning points of the RR-intervals. A signal with AF is likely to have larger values of the first 3 indicators. It is also likely to not have a small or large number of turning points. Thresholds for all 4 indicators are chosen for a given ECG signal, and all 4 indicators must be within/above threshold for an AF call.

If the number of QRS complexes is above 35, Sluter's algorithm is used along with the above-mentioned turning point value. This algorithm is based on using a 10 beat window before any given beat, and calculating the best predictor beat within that window for the given beat. This 10 beat window is moved across the entire signal "yfinal", and the best average predictor beat is found. The error of this predictor beat is calculated, and if it is large-enough and the turning point value is within threshold, AF is called.

Finally, P-waves are searched for. This is done using a template P-wave and correlating it with the average-beat signal before the QRS onset. The maximum value in the signal before the Q wave is found that is also a local maximum, and is taken to be the peak of the proposed p-wave and is used as the correlation point. The standard deviation of the proposed P-wave is also calculated and compared to the standard deviation of the rest of the average-beat signal before the Q-wave. The ratio of the std of the proposed P-wave to the std of the remaining signal is used as a weighting factor in determining the probability that the proposed P-wave is a P-wave. A final statistic is calculated for P-wave probability for which 1 means perfect P-wave, while 0 and negative numbers indicate there is no P-wave.

If the P-wave statistic is below 0.25, AF is automatically called even if it was not called based on the RR-statistic indicators. If the P-wave statistic is above 0.7 and the ratio of standard deviations is large-enough, a signal that was called AF based on the RR-statistics is corrected and called non-AF.

Figure 10:
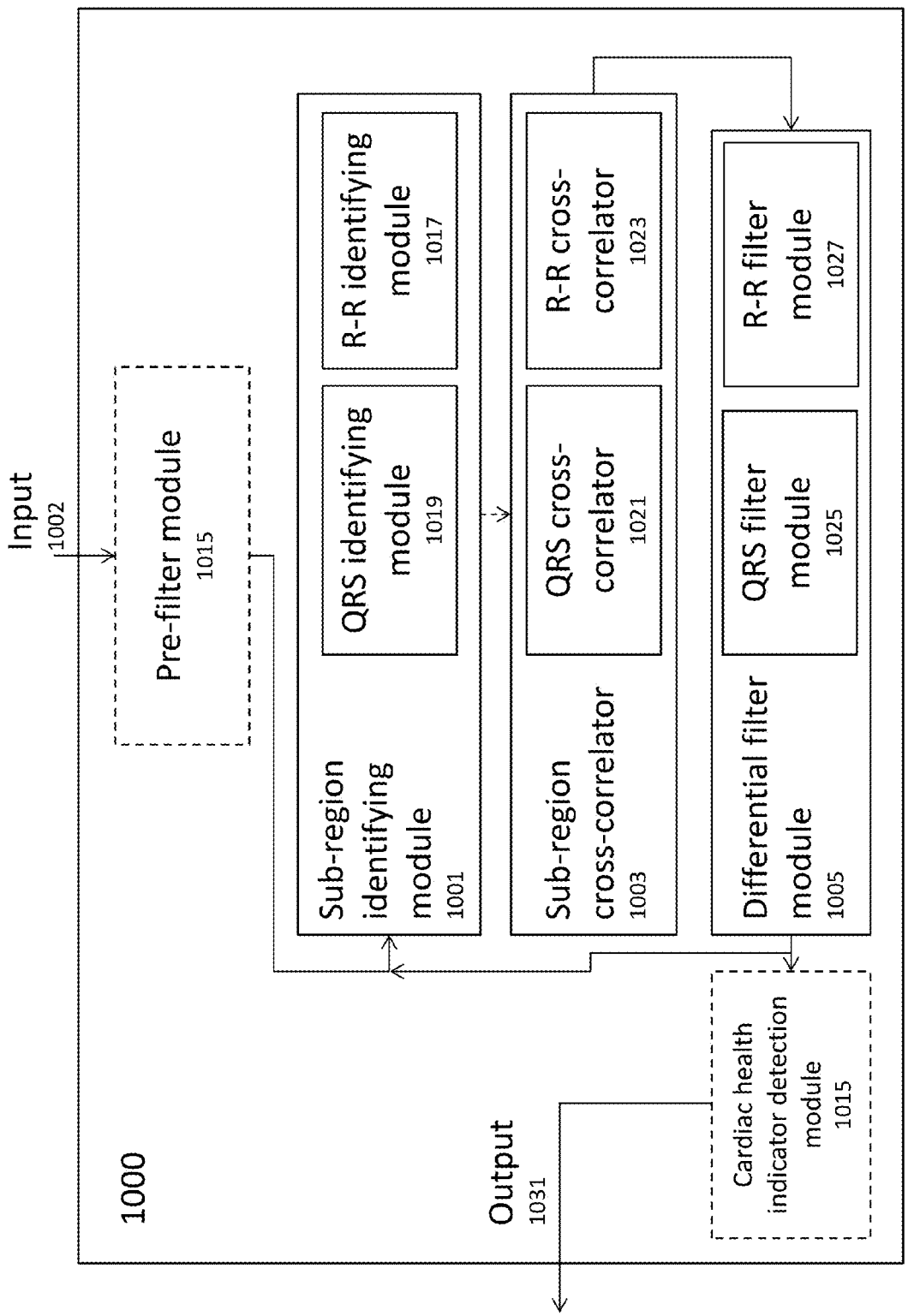
FIG. 10 is a schematic illustration of a system implementing the techniques for extracting an ECG signal from a starting signal by differentially processing correlated sub-regions of ECG signals (e.g., QRS sub-regions and/or R-R sub-regions, etc.).

FIG. 10 illustrates schematically, one example of an apparatus implementing the techniques described above. For example, an apparatus may be a processor having software, hardware and/or firmware (or some combination thereof) for performing the techniques described herein. In some variations the apparatus may be configured as computer code for controlling a processor. The apparatus may also include one or more pairs of electrodes for receiving the starting signal.

In FIG. 10, the input 1002 (e.g., from electrodes, or from a received ECG starting signal) receives a signal that may be optionally pre-processed, e.g., by pre-filter 1015, as mentioned above. The system may also include a sub-region identifying module that reviews the signal being operated on to identify putative sub-regions (e.g., QRS regions). The sub-region identifying module 1001 may be configured to operate on different sub-regions (e.g., QRS, R-R, etc.) or it may include different sub-modules specific to these regions. The sub-region identifying module may be connected to a sub-region cross-correlator 1003 for cross-correlating putative sub-regions. The apparatus may also include on or more memory elements for generating and storing a matrix (e.g., of identified sub-regions); this memory may be modified as the signal is processed. Different matrixes (e.g., putative and/or correlated sub-regions matrixes such as putative and/or correlated QRS matrixes, putative and/or correlated R-R matrix, etc.). The cross-correlator 1003 may include separate sub-region correlators, such as QRS cross-correlator 1021, R-R cross-correlators 1023, etc. The apparatus may also include a differential filter module 1005, which may include sub-modules (QRS filter module 1025, R-R filter module 1027) or the like. In some variations, the apparatus also includes cardiac-health indicator detection modules 1015 configured to determine an indicator of the cardiac health of the patient based on the ECG signal, such as atrial fibrillation. One or more outputs 1031 may also be provided. The output may be a digital output or an indicator output.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all subranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A non-transitory computer-readable storage medium storing a set of instructions capable of being executed by a processor, that when executed by the processor, causes the processor to extract an electrocardiogram (ECG) signal from a signal containing noise by causing the processor to:
   identify putative QRS regions in the signal containing noise;
   cross-correlate the putative QRS regions to determine correlated QRS regions in the signal containing noise;
   de-noise the correlated QRS regions by filtering correlated QRS regions in the signal containing noise using a first filtering regime, wherein the correlated QRS regions are filtered by the first filtering regime in isolation of the entire signal containing noise, and filtering a remainder of the signal containing noise outside of the correlated QRS regions using a second filtering regime that is different from the first filtering regime;
   construct a de-noised ECG signal comprising the filtered correlated QRS regions and the filtered remainder of the signal outside of the correlated QRS regions; and
   present the de-noised ECG signal.

2. The non-transitory computer-readable storage medium of claim 1, wherein the set of instructions, when executed by the processor, further causes the processor to:
   identify putative R-R intervals in the de-noised ECG signal;
   cross-correlate the putative R-R intervals to determine correlated R-R intervals in the de-noised ECG signal; and
   modify the de-noised ECG signal by filtering only the correlated R-R intervals of the de-noised ECG signal with a third filtering regime.

3. The non-transitory computer-readable storage medium of claim 2, wherein the set of instructions causes the processor to identify putative R-R intervals in the de-noised ECG signal by constructing an R-R matrix of normalized R-R intervals from the de-noised ECG signal.

4. The non-transitory computer-readable storage medium of claim 3, wherein the set of instructions causes the processor to cross-correlate the putative R-R intervals to determine correlated R-R intervals in the de-noised ECG signal by cross-correlating every normalized R-R interval in the R-R matrix against every other normalized R-R interval in the matrix.

5. The non-transitory computer-readable storage medium of claim 4, wherein the set of instructions causes the processor to determine correlated R-R intervals when a correlation coefficient threshold between R-R intervals is above an R-R correlation threshold.

6. The non-transitory computer-readable storage medium of claim 5, wherein the R-R correlation coefficient threshold is about 0.7.

7. The non-transitory computer readable storage medium of claim 5, wherein the set of instructions causes the processor to modify the de-noised ECG signal by filtering only the correlated R-R intervals of the de-noised ECG signal with a Principle Component Analysis (PCA) of the correlated R-R intervals.

8. The non-transitory computer-readable storage medium of claim 1, wherein the set of instructions, when executed by the processor, further causes the processor to pre-filter the signal containing noise before identifying putative QRS regions in the signal containing noise.

9. The non-transitory computer-readable storage medium of claim 1, wherein the set of instructions, when executed by the processor, further causes the processor to remove 50 Hz or 60 Hz noise in the signal containing noise before identifying putative QRS regions in the signal containing noise.

10. The non-transitory computer-readable storage medium of claim 1, wherein the set of instructions, when executed by the processor, further causes the processor to perform wavelet filtering on the signal containing noise before identifying putative QRS regions in the signal containing noise.

11. The non-transitory computer-readable storage medium of claim 1, wherein the set of instructions causes the processor to identify putative QRS regions in the signal containing noise by filtering the signal, setting a threshold, and identifying spikes above the threshold as putative R-spike components of putative QRS regions.

12. The non-transitory computer-readable storage medium of claim 11, wherein the set of instructions, when executed by the processor, further causes the processor to calculate a putative heart rate (HR) from the R-spikes and to use the HR to modify the signal containing noise to remove baseline wander.

13. The non-transitory computer-readable storage medium of claim 1, wherein the set of instructions causes the processor to cross-correlate the putative QRS regions to determine correlated QRS regions of the signal containing noise by cross-correlating each putative QRS region with every other putative QRS region.

14. The non-transitory computer-readable storage medium of claim 1, wherein the set of instructions causes the processor to determine correlated QRS regions of the signal containing noise when a peak correlation between a pair of putative QRS regions is above a correlation threshold and their amplitudes vary by less than an amplitude threshold.

15. The non-transitory computer-readable storage medium of claim 14, wherein the correlation coefficient threshold is about 0.8 and the amplitude threshold is about 40%.

16. The non-transitory computer-readable storage medium of claim 1, wherein the set of instructions, when executed by the processor, further causes the processor to indicate that there may be a problem with the signal containing noise when there are fewer than a minimum number of correlated consecutive putative QRS regions.

17. The non-transitory computer-readable storage medium of claim 16, wherein the minimum number of correlated consecutive putative QRS regions is 6.

18. The non-transitory computer-readable storage medium of claim 1, wherein the set of instructions causes the processor to construct the de-noised ECG signal from the signal by removing the correlated QRS regions from the signal containing noise to form a subtracted signal, filtering the correlated QRS regions of the signal using the first filtering regime and filtering the subtracted signal comprising the remainder of the signal outside of the correlated QRS regions using the second filtering regime, and then adding together the filtered correlated QRS regions with the filtered subtracted signal.

19. The non-transitory computer-readable storage medium of claim 1, wherein the set of instructions causes the processor to construct the de-noised ECG signal from the signal by filtering the correlated QRS regions of the signal using the first filtering regime comprising a Principle Component Analysis (PCA).

20. The non-transitory computer-readable storage medium of claim 1, wherein the set of instructions causes the processor to construct the de-noised ECG signal from the signal by filtering the remainder of the signal outside of the correlated QRS regions using the second filtering regime comprising a polynomial fit to the remainder of the signal outside of the correlated QRS regions.

21. The non-transitory computer-readable storage medium of claim 1, wherein the set of instructions causes the processor to present the de-noised ECG signal by displaying the de-noised ECG signal.

22. The non-transitory computer-readable storage medium of claim 1, wherein the set of instructions, when executed by the processor, further causes the processor to determine if the signal is indicative of an atrial fibrillation.

23. The non-transitory computer-readable storage medium of claim 1, wherein the set of instructions, when executed by the processor, further causes the processor to indicate if the signal is indicative of an atrial fibrillation by comparing a beat-to-beat variability of the de-noised ECG signal.

24. The non-transitory computer-readable storage medium of claim 23, wherein the set of instructions, when executed by the processor, further causes the processor to determine a QRS onset, QRS offset, and T-wave offset from an average beat.

25. The non-transitory computer-readable storage medium of claim 1, wherein the set of instructions, when executed by the processor, further causes the processor to calculate an average beat by averaging correlated QRS regions that overlap on either side by correlated R-R intervals to form an intermediate average, and then correlating the intermediate average with correlated QRS regions that overlap on either side by correlated R-R intervals, and averaging those correlated QRS regions that overlap on either side by correlated R-R intervals that correlate with the intermediate average by greater than a correlation coefficient threshold of about 0.85, to form the average beat.

26. A non-transitory computer-readable storage medium storing a set of instructions capable of being executed by a processor, that when executed by the processor, causes the processor to extract an electrocardiogram (ECG) signal from a signal containing noise by causing the processor to:
   identify putative QRS regions in the signal containing noise;
   cross-correlate the putative QRS regions to determine correlated QRS regions of the signal containing noise; and
   construct a de-noised ECG signal from the signal containing noise by differentially filtering the correlated QRS regions of the signal containing noise relative to a remainder of the signal containing noise outside of the correlated QRS regions, wherein the constructed de-noised ECG signal comprises the filtered correlated QRS regions of the signal containing noise and the filtered remainder of the signal containing noise outside of the correlated QRS regions;
   identify putative R-R intervals in the de-noised ECG signal; and
   cross-correlate the putative R-R intervals present the de-noised ECG signal to determine correlated R-R intervals in the de-noised ECG signal; and
   modify the de-noised ECG signal by differentially filtering the correlated R-R intervals of the de-noised ECG signal relative to a remainder of the signal containing noise outside of the correlated R-R intervals.

27. A non-transitory computer-readable storage medium storing a set of instructions capable of being executed by a processor, that when executed by the processor, causes the processor to extract an electrocardiogram (ECG) signal from a signal containing noise by causing the processor to:

identify putative QRS regions in a signal containing noise;
cross-correlate each of the putative QRS regions with each other to identify correlated QRS regions;
filter a portion of the signal containing noise corresponding to the correlated QRS regions in isolation using a first filtering regime;
filter a second portion of the signal containing noise corresponding to a region of the signal excluding the correlated QRS regions with a second filtering regime that is different from the first filtering regime;
construct a de-noised ECG signal comprising the filtered portion of the signal containing noise corresponding to the correlated QRS regions and the filtered portion of the signal containing noise corresponding to a region of the signal excluding the correlated QRS regions;
identify putative R-R intervals in the de-noised ECG signal;
cross-correlate the putative R-R intervals to determine correlated R-R intervals;
modify the first ECG signal by filtering only the portion of the de-noised ECG signal corresponding to the correlated R-R intervals with a third filtering regime; and
display the first ECG signal.

28. A system for extracting ECG information from a signal containing noise, the system comprising:
a QRS identifying module configured to receive an electrical signal and to identify a plurality of putative QRS regions in the signal;
a QRS cross-correlator coupled to the QRS identifying module configured to cross-correlate each of the putative QRS regions with each other;
a QRS filter module coupled to the QRS cross-correlator and configured to modify the signal by differentially filtering correlated QRS regions of the signal containing noise relative to other regions of the signal;
an ECG constructing module coupled to the QRS cross-correlator and configured to construct a de-noised ECG comprising the differentially filtered correlated QRS regions of the signal containing noise relative to other regions of the signal;
an R-R cross-correlator adapted to receive the modified signal from the QRS filter module and to cross-correlate putative R-R intervals in the modified signal with each other; and
an R-R filter module coupled to the R-R cross-correlator and configured to further modify the modified signal by differentially filtering correlated R-R intervals relative to other regions of the modified signal.

29. The system of claim 28, further comprising a pre-filtering module connected to the QRS identifying module and configured to pre-filter the received signal containing noise before it is passed to the QRS identifying module.

30. The system of claim 28, further comprising an atrial fibrillation detection module configured to receive the further modified signal from the R-R filter module and to output an indicator if the further modified signal is indicative of atrial fibrillation.

31. The system of claim 28, wherein the QRS identifying module comprises a R-wave detection module having a band pass filter and moving window integrator.

32. A non-transitory computer-readable storage medium storing a set of instructions capable of being executed by a processor, that when executed by the processor, causes the processor to determine if an electrocardiogram (ECG) signal containing noise is indicative of atrial fibrillation, by causing the processor to:
identify putative QRS regions in a signal;
cross-correlate the putative QRS regions to determine correlated QRS regions of the signal;
construct a de-noised ECG signal from the signal containing noise by differentially filtering the correlated QRS regions of the signal containing noise relative to a remainder of the signal outside of the correlated QRS regions, wherein the constructed de-noised ECG signal comprises the filtered correlated QRS regions of the signal containing noise and the filtered remainder of the signal containing noise outside of the correlated QRS regions;
identify putative R-R intervals in the de-noised ECG signal; and
cross-correlate the putative R-R intervals present the de-noised ECG signal to determine correlated R-R intervals in the de-noised ECG signal;
modify the de-noised ECG signal by differentially filtering the correlated R-R intervals of the de-noised ECG signal relative to a remainder of the signal containing noise outside of the correlated R-R intervals; and
determine if the de-noised ECG signal is indicative of atrial fibrillation.

33. The non-transitory computer-readable storage medium of claim 32, wherein the set of instructions causes the processor to determine if the de-noised ECG signal is indicative of atrial fibrillation by examining a number of turning points of correlated R-R intervals in the de-noised ECG signal.

34. The non-transitory computer-readable storage medium of claim 32, wherein the set of instructions causes the processor to determine if the de-noised ECG signal is indicative of atrial fibrillation by measuring beat-to-beat variability, beat-to-every-other-beat variability, and beat-to-every-third-beat variability.

35. The non-transitory computer-readable storage medium of claim 32, wherein the set of instructions causes the processor to determine if the de-noised ECG signal is indicative of atrial fibrillation by measuring beat-to-beat variability, beat-to-every-other-beat variability, and beat-to-every-third-beat variability and by examining the number of turning points of R-R intervals in the de-noised ECG signal.

36. The non-transitory computer-readable storage medium of claim 32, wherein the set of instructions causes the processor to determine if the de-noised ECG signal is indicative of atrial fibrillation by calculating a plurality of predictor beats from a window of n beats in the de-noised ECG signal as the window is moved though the de-noised ECG signal, where n is greater than three.

37. The non-transitory computer-readable storage medium of claim 32, wherein the set of instructions causes the processor to determine if the de-noised ECG signal is indicative of atrial fibrillation by calculating a plurality of predictor beats from a window of n beats in the de-noised ECG signal as the window is moved though the de-noised ECG signal, where n is about 10 or more.

38. The non-transitory computer-readable storage medium of claim 32, wherein the set of instructions causes the processor to determine if the de-noised ECG signal is indicative of atrial fibrillation by calculating a plurality of predictor beats from a window of n beats in the de-noised ECG signal as the window is moved though the de-noised ECG signal, where n is greater than three and by examining a number of turning points of R-R intervals in the de-noised ECG signal.

39. The non-transitory computer-readable storage medium of claim 32, wherein the set of instructions causes the processor to determine if the de-noised ECG signal is indicative of atrial fibrillation by calculating an average beat from the de-noised ECG signal and correlating a proposed P-wave with the region of the average beat before the QRS onset of the average beat.

40. The non-transitory computer-readable storage medium of claim 39, wherein the set of instructions causes the processor to calculate an average beat by averaging correlated QRS regions that overlap on either side by correlated R-R intervals to form an intermediate average, and then correlating the intermediate average with correlated QRS regions that overlap on either side by correlated R-R intervals, and averaging those correlated QRS regions that overlap on either side by correlated R-R intervals that correlate with the intermediate average by greater than a threshold of about 0.85, to form the average beat.

41. A computer implemented method for extracting an electrocardiogram (ECG) signal from a signal containing noise comprising the steps of:

identifying putative ECG sub-regions in a signal; cross-correlating the putative sub-regions to determine correlated sub-regions of the signal; and constructing a de-noised ECG signal from the signal containing noise by filtering the correlated sub-regions of the signal using a first filtering regime and filtering a remainder of the signal outside of the correlated sub-regions using a second filtering regime that is different from the first filtering regime, wherein the constructed de-noised ECG comprises the filtered correlated sub-regions of the signal using a first filtering regime and the filtered remainder of the signal outside of the correlated sub-regions.

42. A computer implemented method for extracting an electrocardiogram (ECG) signal from a signal containing noise comprising the steps of:

identifying putative QRS regions in a signal; cross-correlating the putative QRS regions to determine correlated QRS regions of the signal; and constructing a de-noised ECG signal from the signal by filtering the correlated QRS regions of the signal using a first filtering regime and filtering a remainder of the signal outside of the correlated QRS regions using a second filtering regime that is different from the first filtering regime, wherein the constructed de-noised ECG comprises the filtered correlated QRS regions of the signal using a first filtering regime and the filtered remainder of the signal outside of the correlated QRS.

\* \* \* \* \*